United States Patent [19]

Bolguslaski et al.

[11] Patent Number: 4,629,688
[45] Date of Patent: Dec. 16, 1986

[54] HOMOGENEOUS SPECIFIC BINDING ASSAY METHOD

[75] Inventors: Robert C. Bolguslaski, Elkhart; Robert J. Carrico, Bremen, both of Ind.; James E. Christner, Ann Arbor, Mich.

[73] Assignee: Miles Laboratories, Inc., Elkhart, Ind.

[21] Appl. No.: 894,836

[22] Filed: Apr. 10, 1978

Related U.S. Application Data

[63] Continuation of Ser. No. 667,996, Mar. 18, 1976, abandoned, which is a continuation-in-part of Ser. No. 572,008, Apr. 28, 1975, abandoned.

[51] Int. Cl.$^4$ ............. G01N 33/54; G01N 33/58; C12N 11/00
[52] U.S. Cl. ................................ 435/7; 435/174; 436/537; 436/544; 436/546
[58] Field of Search .................. 435/7, 174, 177; 436/537, 543, 544, 546

[56] References Cited

U.S. PATENT DOCUMENTS

| | | | |
|---|---|---|---|
| 3,817,837 | 6/1974 | Rubenstein et al. | 195/103.5 R |
| 3,839,153 | 10/1974 | Schuurs et al. | 195/103.5 R |
| 3,880,934 | 4/1975 | Rammler | 195/103.5 A X |
| 3,998,943 | 12/1976 | Ullman | 424/12 |

OTHER PUBLICATIONS

Miles, et al., Labelled Antibodies and Immunological Assay Systems, Nature, vol. 29, 1968 (pp. 186-189).

Primary Examiner—David M. Naff
Attorney, Agent, or Firm—Andrew L. Klawitter

[57] ABSTRACT

A test composition, device, and method for their use in a homogeneous specific binding assay which employs a substance having reactant activity, i.e., a reactant, as a labeling substance in the detection of a ligand in a liquid medium. The test composition and device comprise a conjugate formed of a specific binding substance coupled to the reactant. The reactant advantageously is an enzymatic reactant such as an enzyme substrate or coenzyme. The activity of the conjugated reactant as a constituent of a predetermined reaction is affected by reaction between the specific binding substance in the conjugate and a specific binding counterpart thereto. The presence of a ligand in a liquid medium may be determined using competitive or displacement binding or sequential saturation techniques wherein the specific binding substance in the conjugate is the ligand or a specific binding analog thereof, or using a direct binding technique wherein the specific binding substance is a specific binding partner of the ligand. The effect of the specific binding reaction on the activity of the conjugated reactant is related to the presence or amount of the ligand in the liquid medium tested.

42 Claims, 12 Drawing Figures

HOMOGENEOUS SPECIFIC BINDING ASSAY METHOD

This is a continuation of application Ser. No. 667,996, filed Mar. 18, 1976, now abandoned, which was a continuation-in-part of application Ser. No. 572,008, filed Apr. 28, 1975, now abandoned.

BACKGROUND OF THE INVENTION

1. Field of the Invention

This invention relates to compositions, devices, and methods for determining the presence of a ligand in a liquid medium based on the affinity of the ligand for a specific binding partner thereof. In particular, this invention relates to compositions, devices, and methods for use in specific binding assays which do not require a separation step and which do not employ radioactive materials or modified enzymes as the labeling substance.

The desirability of a convenient, reliable, and non-hazardous means for detecting the presence of low concentrations of substances in liquids is self-evident. This is particularly true in the field of clinical chemistry where constituents of body fluids which may appear in concentrations as low as $10^{-11}$ molar are known to be of pathological significance. The difficulty of detecting such low concentrations is compounded in the field of clinical chemistry where sample size is usually quite limited.

Classically, substances have been detected in liquids based on a reaction scheme wherein the substance to be detected is a necessary reactant. The presence of unknown is indicated by the appearance of a reaction product or the disappearance of a known reactant. In certain instances, such an assay method may be quantitative, based on a measurement of either the rate of appearance of product or disappearance of reactant or measurement of the aggregate amount of product produced or reactant consumed in attaining equilibrium. Each assay reaction system is necessarily either limited to use in the detection of only a small group of substances or is non-specific.

The search for assay systems which are highly specific yet adaptable to the detection of a wide range of substances has evolved the radioimmunoassay. In this system a known amount of a radiolabeled form of the substance to be detected is allowed to compete with the unknown for a limited quantity of antibody specific for the unknown. The amount of the labeled form that becomes bound to antibody varies inversely with the level of unknown present. Inherent in the radioimmunoassay technique is the need to separate the labeled form of substance to be detected which becomes bound to antibody from that which does not become so bound. While various ways of accomplishing the required separation have been developed, as exemplified in U.S. Pat. Nos. 3,505,019; 3,555,143; 3,646,346; 3,720,760; and 3,793,445, all require at least one separate manipulative step, such as filtering, centrifuging, or washing, to insure efficient separation of the bound-labeled form from the unbound-labeled form. The elimination of the separation step would greatly simplify the assay and render it more useful to the clinical laboratory.

The use of radioactive materials in immunoassays has been eliminated to some degree by the use of enzyme-tagged materials in place of radiolabels. As exemplified by U.S. Pat. Nos. 3,654,090 and 3,791,932, the manipulative steps necessary for carrying out the enzyme-tagged immunoassays are for the most part the same as those required in radioimmunoassays and include the cumbersome separation step. An additional disadvantage of using enzyme-tagged materials is that each enzyme used as a tag must be individually chemically modified for use in the formation of the tagged conjugate. The use of other tagging materials has been suggested, such as the use of coenzymes or viruses, Nature 219: 186 (1968) and the use of fluorescent-labels, French Pat. No. 2,217,350, corresponding to U.S. Pat. No. 3,880,934.

2. Description of the Prior Art

While the radiolabeled and enzyme-tagged immunoassays may undergo future improvement in terms of expansion of the range of substances detectable thereby or of simplification of the procedure, by their nature they will always require some type of separation step. Recently, a different approach was disclosed which does not require a separation step and therefore has been referred to as a homogeneous system, in contrast to a heterogeneous system in which separation is essential. U.S. Pat. No. 3,817,837 discloses a competitive binding assay method involving the steps of combining the liquid to be assayed with a soluble complex consisting of an enzyme as a labeling substance covalently bound to the ligand to be detected and with a soluble receptor, usually an antibody, for the ligand; and analyzing for the effect of the liquid to be assayed on the enzymatic activity of the enzyme in the complex.

While this method has the advantage of not requiring a separation step because reaction between the enzyme-bound-ligand complex and the receptor results in inhibition of the enzymatic activity of the enzyme in the complex, the method nonetheless is severely restricted in its ability to be adapted to widely varied assay requirements. For instance, it is clearly essential that in the fabrication of the enzyme-bound-ligand complex, the substance or ligand to be detected must be coupled to the enzyme in a carefully controlled manner so that the coupling site is close to the enzymatically active site on the enzyme. This is required in order that upon reaction between the complexed ligand and the receptor, the enzymatically active site is blocked. Enzymes vary greatly in their size, ranging in molecular weight from about 10,000 to 1,000,000. Thus, for a receptor in the form of an antibody having a molecular weight of between 150,000 and 300,000 to be capable of physically blocking the active site on an average enzyme of 500,000 molecular weight or greater, the coupling site must be precisely controlled. Due to the complex chemical structure of enzymes, precise control of such chemical linkage is indeed difficult, and one would expect that even upon screening a wide variety of enzymes only a small number would be found to be of use in this homogeneous assay system.

Moreover, it is critical for the purpose of obtaining quantitative test results to precisely control the ratio of the number of enzymes to the number of ligands in each enzyme-bound-ligand complex. Here also, the complex peptide structure of enzymes makes such control difficult. It would again be expected that only a small number of enzymes would have suitable molecular structure to ensure necessary control of the ligand/enzyme ratio.

The prior art homogeneous assay method is stated to involve an enzyme amplification and thus to be highly sensitive. However, since the labeling substance, namely the enzyme, is itself the limiting factor determining the sensitivity of the prior art assay method, the versatility of the method is severely restricted. The sensitivity is clearly limited to the catalytic activity of the particular enzyme in the enzyme-bound-ligand conjugate. The versatility of the prior art method is therefore restricted not only by the coupling requirements for formation of a useful conjugate but also by the dependence of the sensitivity of the assay that employs such conjugate on the activity of the particular conjugated enzyme.

An additional disadvantage of the prior art homogeneous assay method arises in its application to the testing of biological fluids such as urine and serum. It is to be expected that significant amounts of the enzyme species comprised in the enzyme-bound-ligand conjugate may appear in the fluid sample to be tested thereby creating an uncontrollable background activity which would severely affect the accuracy of the assay method. Therefore, in order to form an assay system that is useable in testing biological fluids of humans or animals, exotic enzymes not endogenous to such fluids must be selected for use in forming the enzyme-bound-ligand conjugate with the result that the versatility of the assay method is even further restricted.

It is therefore an object of the present invention to provide a novel test composition, device, and method for detecting a ligand in a liquid which do not require a separation step and which do not employ inconvenient radioactive materials or modified enzymes as the labeling substance.

Further, it is an object of the present invention to provide a homogeneous specific binding assay method and system which are more versatile and convenient than those of the prior art.

Another object of the present invention is to provide a homogeneous specific binding assay method and system which employ a labeling substance which is capable of being coupled to the ligand or to a specific binding partner thereof more conveniently than can the enzyme of the prior art method.

A further object of the present invention is to provide a homogeneous specific binding assay method and system which employ a conjugate comprising a labeling substance whose activity is more readily affected by a specific binding reaction than is the enzyme of the prior art method.

It is also an object of the present invention to provide a homogeneous specific binding assay method and system which employ a conjugate comprising a labeling substance any change in the activity of which is more conveniently detectable using a wide variety of sensitive reaction systems than is any change in the activity of the enzyme in the prior art method.

It is a further object of the present invention to provide a homogeneous specific assay method and system which are more readily applicable to the testing of biological fluids than those of the prior art.

SUMMARY OF THE INVENTION

The present invention provides a highly convenient, versatile, and sensitive homogeneous specific binding assay method and system based on the use of, as labeling substance, a substance which exhibits given reactant activity as a constituent of a predetermined reaction, such substance being referred to herein as the reactant. The method is based, in part, on the fact that the reaction between a ligand and a specific binding partner thereof to one of which the reactant is coupled alters the activity of the reactant in the predetermined reaction, which reaction thus serves as means for monitoring the specific binding reaction. In view of this basic phenomenon, various manipulative schemes involving various test compositions and devices may be employed in performing the method of the present invention. The preferred fundamental manipulative schemes are the direct binding technique and the competitive binding technique.

In the direct binding technique, a liquid medium suspected of containing the ligand to be detected is contacted with a conjugate comprising the reactant coupled to a specific binding partner of the ligand, and thereafter any change in the activity of the reactant is assessed. In the competitive binding technique, the liquid medium is contacted with a specific binding partner of the ligand and with a conjugate comprising the reactant coupled to one or both of the ligand or a specific binding analog thereof, and thereafter any change in the activity of the reactant is assessed. In both techniques, the activity of the reactant is determined by contacting the liquid medium with at least one reagent which forms, with the reactant, the predetermined monitoring reaction. Qualitative determination of the ligand in the liquid medium involves comparing a characteristic, usually the rate, of the resulting reaction to that of the monitoring reaction in a liquid medium devoid of the ligand, any difference therebetween being an indication of a change in activity of the reactant. Quantitative determination of the ligand in the liquid medium involves comparing a characteristic of the resulting reaction to that of the monitoring reaction in liquid media containing known amounts of the ligand.

The monitoring reaction preferably is enzyme-catalyzed. Usually, a monitoring reaction is selected which is highly sensitive to the reactant in the conjugate. Luminescent or fluorescent reaction systems are very useful in this regard. Particularly preferred are cyclic reaction systems, especially those in which the reactant is the cycled material. Of the preferred cyclic reaction systems, those which are enzyme-catalyzed are particularly advantageous. The reactant in the conjugate is usually an enzymatic reactant, such as an enzyme substrate or, as is particularly preferred, a coenzyme, and preferably has a molecular weight of less than 9000.

DESCRIPTION OF THE PREFERRED EMBODIMENTS

Figure 1:
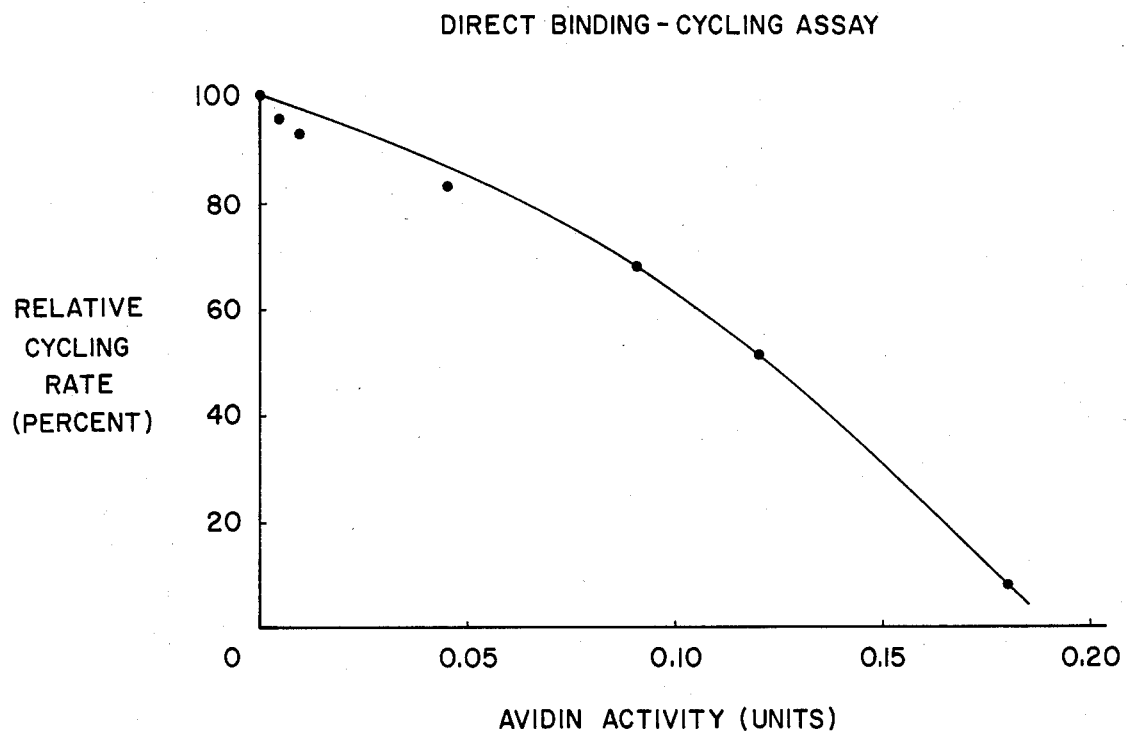
FIG. 1 is a graphical representation of the effect of various levels of a ligand on the aggregate reaction rate in a direct binding-cycling assay technique.

In the context of this disclosure, the following terms shall be defined as follows: ligand is the substance, or group of substances, whose presence or the amount thereof in a liquid medium is to be determined; specific binding partner of the ligand is any substance, or group of substances, which has a specific binding affinity for the ligand to the exclusion of other substances; and specific binding analog of the ligand is any substance, or group of substances, which behaves essentially the same as the ligand with respect to the binding affinity of the specific binding partner for the ligand.

In general, the components of the specific binding reaction, i.e., the liquid medium suspected of containing the ligand, the conjugate, and/or a specific binding partner of the ligand, may be combined in any amount, manner, and sequence, provided that the activity of the reactant in the conjugate is measurably altered when the liquid medium contains the ligand in an amount or concentration of significance to the purpose of the assay. Preferably, all of the components of the specific binding reaction are soluble in the liquid medium, thus providing a homogeneous assay system. However, a heterogenous assay system wherein the conjugate or a specific binding partner of the ligand is insoluble may be employed if desired.

Where a direct binding technique is used, the components of the specific binding reaction are the liquid medium suspected of containing the ligand and a quantity of a conjugate comprising the reactant coupled to a specific binding partner of the ligand. The activity of the conjugated reactant on contact with the liquid medium varies inversely with the extent of binding between the ligand in the liquid medium and the specific binding partner in the conjugate. Thus, as the amount of ligand in the liquid medium increases, the activity of the conjugated reactant decreases. To obtain quantitative results, the amount of the specific binding partner contacted with the liquid medium is usually in excess of that capable of binding with all of the ligand thought to be present in the liquid medium during the time that the conjugate and the liquid medium are in contact prior to completion of the assessment of any charge in activity of the conjugated reactant. In practice, an amount of the specific binding partner is chosen according to the above-mentioned criterion based on an estimation of the largest amount of the ligand which is likely to be present in the liquid medium. A direct binding technique is particularly useful in detecting high molecular weight ligands which have specific binding partners that are smaller than themselves.

Where a competitive binding technique is used, the components of the specific binding reaction are the liquid medium suspected of containing the ligand, a quantity of a conjugate comprising the reactant coupled to the ligand or a specific binding analog of the ligand, and a quantity of a specific binding partner of the ligand. The specific binding partner is contacted substantially simultaneously with both the conjugate and the liquid medium. Since any ligand in the liquid medium competes with the ligand or specific binding analog thereof in the conjugate for binding with the specific binding partner, the activity of the conjugated reactant on contact with the liquid medium varies directly with the extent of binding between the ligand in the liquid medium and the specific binding partner. Thus, as the amount of the ligand in the liquid medium increases, the activity of the conjugated reactant increases. To obtain quantitative results, the amount of the specific binding partner contacted with the conjugate and the liquid medium is usually less than that capable of binding with all of the ligand thought to be present in the liquid medium and all of the ligand or ligand analog in conjugated form in the time that the specific binding partner, the conjugate, and the liquid medium are in contact prior to completion of the assessment of any change in activity of the conjugated reactant. In practice, an amount of the specific binding partner is chosen according to the above-mentioned criterion based on an estimation of the largest amount of the ligand which is likely to be present in the liquid medium. Usually, the amount of the ligand or ligand analog in conjugated form which is contacted with the liquid medium does not exceed the smallest amount of the ligand to be tested for in the liquid medium. A competitive binding technique is particularly useful in detecting ligands which have specific binding partners that are larger than themselves.

A variation of the competitive binding technique is the displacement binding technique wherein the conjugate is contacted first with the specific binding partner of the ligand and thereafter with the liquid medium. Competition for the specific binding partner then occurs. In such a method, the amount of the conjugate contacted with the specific binding partner is usually that which comprises the ligand or analog thereof in excess of that capable of binding with the amount of the specific binding partner present during the time that the conjugate and the specific binding partner are in contact prior to contact with the liquid medium suspected of containing the ligand. This order of contact may be accomplished in either of two convenient ways. In one method, the conjugate is contacted with the specific binding partner in a liquid environment prior to contact with the liquid medium suspected of containing the ligand. In the second method, the liquid medium suspected of containing the ligand is contacted with a complex comprising the conjugate and the specific binding partner, the specific binding substance in the conjugate and the specific binding partner being reversibly bound to each other. The amount of the conjugate that becomes bound to the specific binding partner in the first method, as well as the amount thereof which is in complexed form in the second method, is usually in excess of that capable of being displaced by all of the ligand in the liquid medium in the time that the specific binding partner, or complex, and the medium are in contact prior to the completion of the assessment of any change in the activity of the conjugated reactant.

Another variation of the competitive binding technique is the sequential saturation technique wherein the components of the specific binding reaction are the same as those used in the competitive binding technique, but the order of addition or combination of the components and the relative amounts thereof used are different. Following a sequential saturation technique, the specific binding partner of the ligand is contacted with the liquid medium suspected of containing the ligand for a period of time prior to the contact of said liquid medium with the conjugate. The amount of the specific binding partner contacted with the liquid medium is usually in excess of that capable of binding with all of the ligand thought to be present in the liquid medium in the time that the specific binding partner and the liquid medium are in contact prior to the time that the liquid medium is contacted with the conjugate. Further, the amount of the ligand or ligand analog in conjugated form is usually in excess of that capable of binding with the remaining unbound amount of the specific binding partner during the time that the liquid medium and the conjugate are in contact prior to the completion of the assessment of any change in activity of the conjugated reactant. In practice, the amounts of the specific binding partner and of the ligand or ligand analog in conjugated form are chosen according to the above-mentioned criterion by estimating the largest amount of the ligand likely to be present in the liquid medium.

It is contemplated that manipulative schemes involving other orders of addition and other relative amounts of the specific binding reaction components may be devised for carrying out a homogeneous specific binding assay without departing from the inventive concept embodied herein.

The step of assessing any change in activity of the conjugated reactant as a constituent of the predetermined monitoring reaction is conveniently accomplished by contacting the specific binding reaction mixture with at least one substance which forms with the conjugated reactant, the monitoring reaction, and determining the effect of the specific binding reaction on a characteristic of such reaction. The monitoring reaction may comprise a single chemical transformation or a plurality or series of chemical transformations. Unless otherwise specified, the term "reaction system" as used herein refers to the whole or a portion of the predetermined monitoring reaction.

Where an enzyme-catalyzed reaction system is used, it includes, in addition to the conjugated reactant, at least one enzyme and may include one or more enzymatic reactants such as substrates and coenzymes. Such enzyme-catalyzed reaction system may comprise a single simple enzymatic reaction or a complex series of enzymatic and non-enzymatic reactions. For instance, the enzyme-catalyzed reaction system may consist of a single enzyme-catalyzed degradation or dissociation reaction. In such a system, the conjugated reactant is the enzyme substrate which undergoes degradation or dissociation, and the only component of the reaction system necessary to be contacted with the specific binding reaction mixture is an enzyme which catalyzes the degradation or dissociation reaction. A more complex enzyme-catalyzed reaction system may consist of a single enzymatic reaction involving two or more reactants or may consist of a series of reactions involving several reactants, at least one of which reactions is enzyme-catalyzed. In such a system, the conjugated reactant would be one of the enzymatic reactants in the enzyme-catalyzed reaction and the specific binding reaction mixture would be contacted with the appropriate enzyme and reactant constituents, other than that in the conjugate, which are necessary to provide the selected enzyme-catalyzed reaction system.

It is further contemplated that the enzyme-catalyzed reaction system may comprise a biochemical system as complex as the metabolic system of a biological cell such as a microorganism. For example, a nutrient substance essential to the growth of a particular microorganism may be selected as the reactant in the conjugate. Any change in the activity of the reactant would cause a change in a growth characteristic of the microorganism when such microorganism would be placed in an environment wherein the only source of the reactant nutrient substance is the conjugate. Thus, for example, a change in the rate of microorganism growth when contacted with the specific binding reaction mixture would indicate the presence of the ligand therein.

The appropriate reaction constituents which form, together with the reactant in the conjugate, the monitoring reaction may be contacted with the specific binding reaction mixture singularly or in any combination either prior to, simultaneous with, or subsequent to initiation of the specific binding reaction. After initiation of the specific binding reaction, the reaction mixture, which may include any or all of the necessary components for the monitoring reaction is usually incubated for a predetermined period of time before assessing any change in the activity of the reactant in the conjugate. After the incubation period, any components which are necessary for the monitoring reaction and which are not already present in sufficient quantities in the reaction mixture are added thereto, and any effect on the monitoring reaction is assessed as an indication of the presence or amount of the ligand in the liquid medium.

In the situation where the ligand is absent from the liquid medium, or is present in an insignificantly small amount, the predetermined monitoring reaction exhibits a relatively constant character. When the ligand is present in the liquid medium, at least one characteristic or property of the monitoring reaction is altered. Generally, the activity of the conjugated reactant is defined as the extent or rate at which the reactant is capable of participating in the monitoring reaction. Thus, the character of the monitoring reaction is altered by the presence of the ligand in the liquid medium, usually with respect to either the aggregate reaction rate thereof or the equilibrium quantity of one or more reaction products produced thereby. In the usual case, the ability of the conjugated reactant to participate in the monitoring reaction is decreased upon reaction between the specific binding substance to which it is conjugated and a specific binding counterpart of such specific binding substance, that is, the conjugate in its free state is more active in the monitoring reaction than in its bound state. The relative amounts of free and bound conjugate present after the incubation of the specific binding reaction are a function of the amount of ligand in the liquid medium and are determinative of the effect on the monitoring reaction.

When the change in the aggregate reaction rate of the monitoring reaction is the characteristic used to determine the presence of the ligand, as is preferred, such rate is usually determined by measuring the rate of disappearance of a reactant or the rate of appearance of a reaction product. Such measurement can be accomplished by a wide variety of methods including the conventional chromatographic, gravimetric, potentiometric, spectrophotometric, fluorometric, turbidimetric, and volumetric analysis techniques. Since the present method is primarily designed for the detection of low concentrations of ligands, highly sensitive reaction systems have been developed for use in conjunction with the novel specific binding reaction system.

One preferred form of the monitoring reaction includes a luminescent reaction system, preferably enzyme-catalyzed, such as a reaction exhibiting the phenomenon of bioluminescence or chemiluminescence. The reactant in the conjugate may be a reactant in either the light-producing reaction or a reaction which is preliminary to an enzymatic or non-enzymatic luminescent reaction. Any change in the activity of the conjugated reactant resulting from the specific binding reaction causes a change in the rate of light production or in the total amount, peak intensity, or character of the light produced. Examples of luminescent reaction systems are given in Table A in which the following abbreviations are used:

ATP: adenosine triphosphate
AMP: adenosine monophosphate
NAD: nicotinamide adenine dinucleotide
NADH: reduced nicotinamide adenine dinucleotide
FMN: flavin mononucleotide
FMNH$_2$: reduced flavin mononucleotide
hν: electromagnetic radiation, usually in the infrared, visible, or ultraviolet region Kries, P. *Purification and Properties of Renilla Luciferase*, doctoral thesis University of Georgia (1967).
*Am. J. Physiol.* 41: 454 (1916).
*Biol. Bull.* 51: 89 (1926).
*J. Biol. Chem.* 243: 4714 (1968).

Another type of preferred, sensitive, monitoring reaction involves the phenomenon of fluorescence and is enzyme-catalyzed. In such a reaction system the reactant in the conjugate is a substrate in an enzymatic reaction which produces a product which has fluorescent properties that differ from those of the conjugated substrate. Any change in the activity of the conjugated enzymatic reactant resulting from the specific binding reaction causes a change in the fluorescent properties of the reaction mixture. A general reaction scheme for such an enzyme-catalyzed reaction system is as follows:

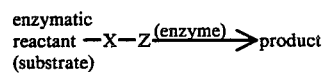

wherein X is an enzyme-cleavable bond or linking group, such as an ester or amido group, and Z is a spe-

TABLE A

| Luminescent Reaction System | Conjugated Reactant |
|---|---|
| A. ATP + reduced luciferin $\xrightarrow{\text{luciferase (fire fly)}}$ hν + AMP + oxidized luciferin | ATP or reduced luciferin |
| B. FMNH$_2$ + long-chain aldehyde + O$_2$ $\xrightarrow{\text{luciferase (P. fisheri)}}$ hν + FMN + long-chain acid + H$_2$O | FMNH$_2$ or long-chain aldehyde |
| C. (1) NADH + FMN + H⊕ $\xrightarrow{\text{NADH dehydrogenase}}$ NAD + FMNH$_2$ | NADH or FMN |
| (2) FMNH$_2$ + long-chain aldehyde + O$_2$ $\xrightarrow{\text{luciferase (P. fisheri)}}$ hν + FMN + long-chain acid + H$_2$O | |
| D. (1) 3′,5′-adenosine diphosphate + reduced luciferin sulfate $\xrightarrow{\text{sulfate transferase}}$ adenosine-3′-phosphate-5′-phosphosulfate + reduced luciferin | 3′5′-adenosine diphosphate or reduced luciferin |
| (2) reduced luciferin + O$_2$ ⟶ hν + oxidized luciferin | |
| E. reduced luminol + H$_2$O$_2$ $\xrightarrow{\text{peroxidase*}}$ hν + oxidized luminol + H$_2$O | reduced luminol |
| F. reduced pyrogallol + H$_2$O$_2$ $\xrightarrow{\text{peroxidase*}}$ hν + oxidized pyrogallol + H$_2$O | reduced pyrogallol |
| G. reduced luminol + O$_2$ $\xrightarrow{\text{oxygenase}}$ hν + oxidized luminol | reduced luminol |
| H. reduced pyrogallol + O$_2$ $\xrightarrow{\text{oxygenase}}$ hν + oxidized pyrogallol | reduced pyrogallol |
| I. isoluminol + H$_2$O$_2$ $\xrightarrow{\text{lactoperoxidase}}$ hν + aminophthalate + N$_2$ | isoluminol |
| J. isoluminol + KO$_2$ ⟶ hν + aminophthalate + N$_2$ | isoluminol |

*or catalase

Further details and discussion concerning luminescent reaction systems which may be used in the present method may be found in the following references:
*J. Biol. Chem.* 236: 48 (1961).
*J. Amer. Chem. Soc.* 89: 3944 (1967).
cornier et al., Bioluminescence in Progress, ed. Johnson et al., Princeton University Press (New Jersey, 1966) pp. 363–84.

cific binding substance which, depending upon the specific binding reaction technique used, is the ligand, a specific binding analog of the ligand, or a specific binding partner of the ligand. Specific conjugates which may be used in this type of reaction system are various enzyme-cleavable derivatives of fluorescein, umbelliferone, 3-indole, β-naphthol, 3-pyridol, resorufin, rhodamine B, and so forth. Examples of possible structural formulas of such derivatives are as follows:

| Derivative | Formula |
|---|---|
| fluorescein | $R^1$ ... $R^2$ (structure) |
| umbelliferone | $R^2$ ... $R^3$ (structure) |
| 3-indole | $R^2$ (structure) |
| β-naphthol | $R^2$ (structure) |
| 3-pyridol | $R^2$ (structure) |
| resorufin | $R^2$ (structure) | wherein $R^1$ is —OH or —X—Z (as defined above in this paragraph), $R^2$ is —X—Z, and $R^3$ is —H or —$CH_3$.

A reaction system which is particularly preferably for use in monitoring the novel specific binding reaction of the present invention is a cyclic or cycling reaction system. Such a reaction system is one in which a product of a first reaction is a reactant in a second reaction, which second reaction has as one of its products a substance that is also a reactant in the first reaction.

The following diagram illustrates a model of a cyclic reaction system:

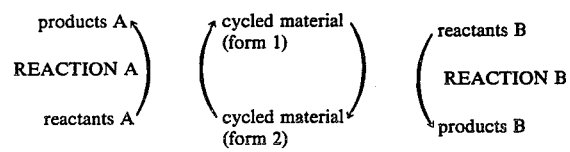

In the above model cyclic reaction system, a small amount of cycled material, if provided with sufficient amounts of reactants A and B, will generate large amounts of products A and B. Since the rate and amount of product produced by the reactions constituting the cyclic reaction system is highly sensitive to the amount of cycled material present, it is most preferred to use the cycled material as the reactant in the conjugate of the present invention. Examples of cycling reaction systems contemplated for use in conjuction with the novel specific binding reaction system of the present invention are given in Tables B, C, and D.

TABLE B product A ← / NAD* \ ← reactant B
enzyme  enzyme
reactant A / \ NADH** / product B

| reaction | reactant A or product B | enzyme | reactant B or product A |
|---|---|---|---|
| 1 | lactaldehyde | alcohol dehydrogenase | propanediol |
| 2 | α-ketoglutarate + $NH_3$ | glutamic dehydrogenase | glutamate |
| 3 | oxaloacetate | malic dehydrogenase | malate |
| 4 | acetaldehyde | alcohol dehydrogenase | ethanol |
| 5 | α-ketoglutarate + $CO_2$ | isocitric dehydrogenase | isocitrate |
| 6 | dihydroxyacetone phosphate | α-glycerol phosphate dehydrogenase | L-α-glycerol phosphate |
| 7 | pyruvate | lactic dehydrogenase | lactate |
| 8 | 1,3-diphosphoglycerate | glyceraldehyde-3-phosphate dehydrogenase | glyceraldehyde-3-phosphate + phosphate |

*nicotinamide adenine dinucleotide
**reduced NAD

TABLE C product A ← / NADP* \ ← reactant B
enzyme  enzyme
reactant A / \ NADPH** / product B

| reaction | reactant A or product B | enzyme | reactant B or product A |
|---|---|---|---|
| 1 | 6-phosphogluconate | glucose-6-phosphate dehydrogenase | glucose-6-phosphate |
| 2 | oxidized glutathione | glutathione reductase | reduced glutathione |
| 3 | p-benzoquinone | quinone reductase | hydroquinone |
| 4 | nitrate | nitrate reductase | nitrite |
| 5 | α-ketoglutarate + $NH_3$ | glutamic dehydrogenase | glutamate |

*nicotinamide adenine dinucleotide phosphate
**reduced NADP

It should be noted that the cyclic reaction systems illustrated in Tables B and (comprise the combination of any one of the reactions listed in the respective tables with any other reaction listed therein. For example, reaction 1 in Table B may be paired with any one of reactions 2–8 to form a useful cyclic reaction system. Thus, Tables B and C represents respectively 56 and 20 possible cyclic reaction system for use in the present invention.

In addition to the cyclic reaction systems represented in Tables B and C, it is contemplated that one of the reactions in the cyclic reaction system may involve the enzymatic or non-enzymatic conversion of a spectrophotometric indicator, preferably colorimetric. In such a system, any change in the reaction or cycling rate would be reflected in a change in the spectrophotometric properties of the indicator. Using the preferred colorimetric indicators such change would be a color change. An example of a cyclic reaction system involving a conversion of an indicator is the system produced by combining one of the reactant B-product B reactions from Table B with a reaction comprising an oxidation-reduction indicator and an electron transfer agent. As electron transfer agent, phenazinemethosulfate may be used. Useful indicators include the oxidized forms of nitrotetrazolium, thiazoyl blue, and dichlorophenolindophenol.

TABLE D

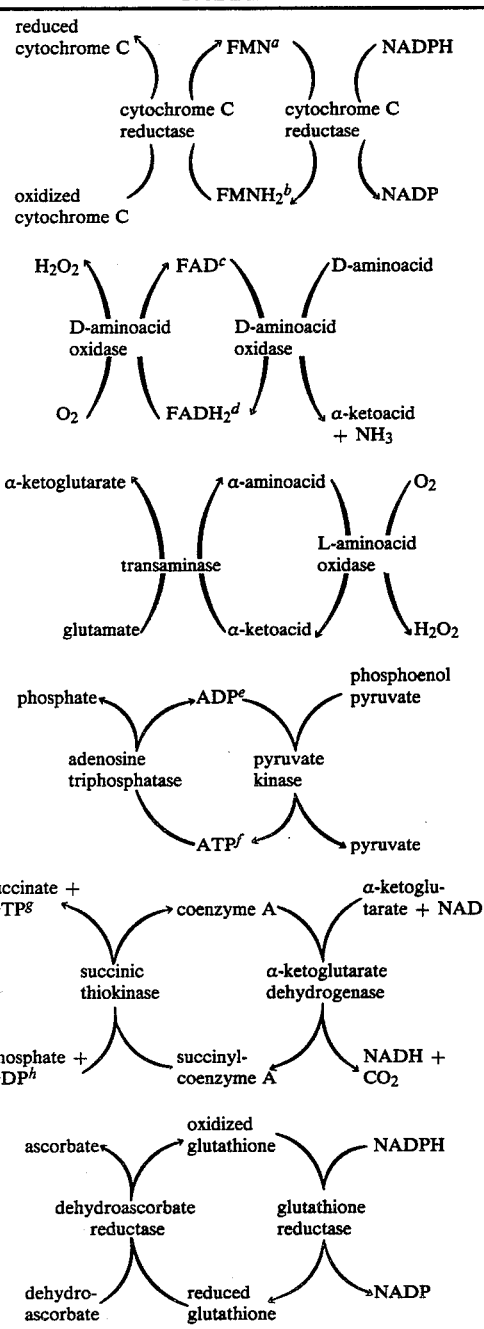

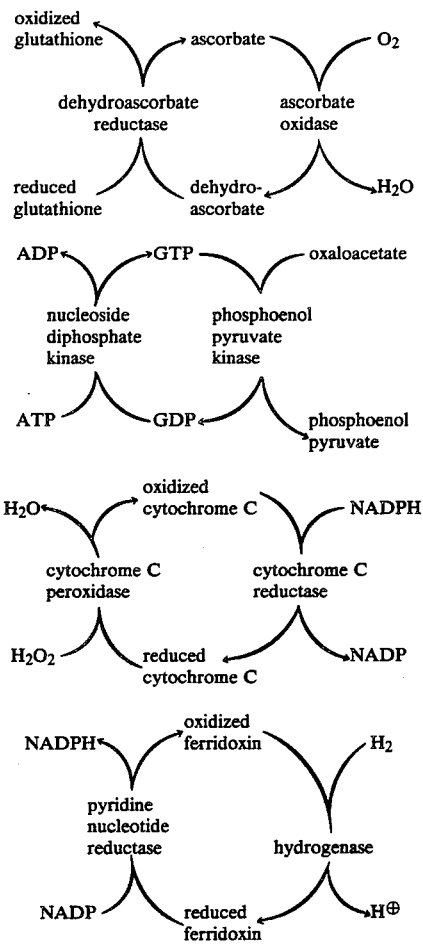

[a] flavin mononucleotide
[b] reduced FMN
[c] flavin adenine dinucleotide
[d] reduced FAD
[e] adenosine
[f] adenosine triphosphate
[g] guanosine triphosphate
[h] guanosine diphosphate In forming any of the cyclic reaction systems illustrated in Tables B, C, and D, where a component in the reaction system is in an ionic form, it may of course be added in a salt or acid form which is ionizable upon contacting the liquid medium. A water soluble salt or acid of such component is usually preferred.

It is also contemplated than an exponential cyclic reaction system may be included in the monitoring reaction system. An example of an exponential cyclic reaction system is as follows:

$$AMP + ATP \xrightarrow{myokinase} 2\ ADP$$

$$ADP + PEP \xrightarrow{pyruvate\ kinase} ATP + pyruvate$$

Such a cyclic reaction is autocatalytic in the sense that during each cycle the amount of cycled material is doubled. The cycling rate therefore increases exponentially with time and affords a high degree of sensitivity. Further details and discussion relating to such cyclic reactions may be found in *J. Biol. Chem.* 247; 3558–70 (1972).

Where a cyclic reaction system is used as a means of assessing any change in activity of the conjugated reactant, the rate of disappearance of a reactant or rate of appearance of a reaction product can be determined by conventional techniques or by using one or more additional cycling systems followed by a conventional determination of the aggregate reaction rate.

The use of a cyclic reaction system in conjunction with the specific binding reaction system provides a high degree of assay versatility as well as sensitivity. A single reactant-specific binding substance conjugate may be used with a multiplicity of reactions to form cyclic systems which have sensitivities varying over a wide range and which provide a wide variety of responses detectable by the senses or artificial means. Such versatility is lacking in the homogeneous enzymatic assay system of the prior art.

While unnecessary in the preferred embodiment of the present invention, it may be desirable to employ a heterogenous assay technique even where the presence of the ligand in the liquid medium effects the activity of the conjugated reactant. Such a situation may present itself where a heterogeneous system offers particular convenience. Certain heterogeneous systems have the ability to increase the effective concentration of the ligand in the assay system, thus increasing sensitivity. An example of such a heterogeneous system is that which employs a column device containing an insoluble matrix comprising either the conjugate of the present invention or a specific binding partner of the ligand, depending on the particular manipulative format selected. All other heterogeneous assay methods employing radio-labeled or enzyme-tagged materials as a labeling substance may also be followed using the reactant of the present invention as the labeling substance.

The present invention may be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in function terms, is usually selected from the group consisting of antigens and antibodies thereto; haptens and antibodies thereto; and hormones, vitamins, metabolites and pharmacological agents, and their receptors and binding substances. Specific examples of ligands which may be detected using the present invention are hormones such as insulin, chorionic gonadotropin, thyroxine, liothyronine, and estriol, antigens and haptens such as ferritin, bradykinnin, prostaglandins, and tumor specific antigens; vitamins such as biotin, vitamin $B_{12}$, folic acid, vitamin E, and ascorbic acid; metabolites such as 3', 5' adenosine monophosphate and 3', 5' guanosine monophosphate; pharmacological agents such as dilantin, digoxin, morphine, digitoxin, and barbiturates; antibodies such as microsomal antibody and antibodies to hepatitis and allergens; and specific binding receptors such as thyroxine binding globulin, avidin, intrinsic factor, and transcobalamine.

In general, it is preferred that the conjugate comprise the reactant coupled to the smaller of the ligand and its selected specific binding partner. It is preferred to use a direct binding technique to detect the ligand where the molecular weight of the selected specific binding partner is about one-tenth that of the ligand or less. Thus, where the ligand to be detected is an antibody or a specific binding receptor, it is preferred to follow a direct binding technique wherein the conjugate comprises an enzymatic reactant coupled to an antigen or hapten to the antibody or a lower molecular weight binding partner of the receptor. Where the molecular weight of the selected binding partner is ten or more times larger than that of the ligand to be detected, as when an antigen, hapten, hormone, vitamin, metabolite or pharmacological agent is to be detected, it is particularly advantageous to employ a competitive binding or sequential saturation technique in which the conjugate comprises the reactant coupled to the smaller ligand.

In the conjugate of the present invention, the reactant is coupled or bound to a specific binding substance, which is the ligand, a specific binding analog of the ligand, or a specific binding partner of the ligand depending upon the assay scheme selected, such that a measurable amount of activity of the reactant is retained. The bond between the reactant and the specific binding substance is usually substantially irreversible under the conditions of the assay such as where the monitoring reaction in which the reactant has activity is not designed to chemically destroy such bond as in the above-mentioned luminescent and cyclic reaction systems. However, in certain instances such bond is by design destroyed or otherwise affected by the selected monitoring reaction as a means for assessing the change in reactant activity. Such a case is the enzymatic fluorescent substrate reaction systems referred to previously herein.

The reactant may be directly coupled to the specific binding substance so that the molecular weight of the conjugate is less than or equal to the aggregate molecular weight of the reactant and the specific binding substance. Usually, however, the reactant and the specific binding substance are linked by a bridge group comprising between 1 and 50, and preferably between 1 and 10, carbon atoms or heteroatoms such as nitrogen, oxygen, sulfur, phosphorus and so forth. Examples of a bridge group comprising a single atom would be a methylene group (one carbon atom) and an amino group (one heteroatom). The bridge group usually has a molecular weight not exceeding 1000 and preferably less than 200. The bridge group comprises a chain of carbon atoms or heteroatoms, or a combination of both, and is joined to the reactant and the specific binding substance, or active derivative thereof, by a connecting group usually in the form of an ester, amido, ether, thioester, thioether, acetal, methylene, or amino group.

The reactant in the conjugate of the present invention may be any substance which has given (i.e. fixed or known) reactant activity as a constituent of a predetermined monitoring reaction. More particularly, for the purposes of this disclosure, the terms "reactant" and "substance having reactant activity" refer to any chemical substance which is capable of undergoing a finite measurable chemical transformation which yields one or more products different from itself and which results upon interaction of said reactant with reaction-initiating means, such as a chemical substance (i.e. another reactant, a catalyst, or other type of material which participates in such chemical transformation), electromagnetic radiation, thermal energy, or sonic energy. The class of substances defined herein as "reactants" therefore includes conventional inorganic and organic reagents and various biochemical materials, but excludes such materials as catalysts, including enzymes, and radioactive isotopes which are not reactants in the monitoring reaction. It will be recognized that while a particular chemical substance may be classified in several different catagories because it is able to function in several ways depending on its chemical environment, it is the activity of such substance with respect to the selected monitoring reaction referred to herein which shall govern which functional identity such substance shall have in the context of this disclosure.

Preferably, the reactant is an enzymatic reactant such as an enzyme substrate, a coenzyme, or an active modification or derivative thereof. An enzyme substrate is a compound or moeity capable of undergoing a chemical transformation that is catalyzed by an enzyme. Where a substrate is employed as the conjugated reactant, the preferred molecular weight thereof is less than 9000 and preferably less than 5000. Substrates of such size, because of their lack of molecular complexity, are most convenient for use in the fabrication of the conjugate. Moreover, the activity of such substrates when coupled to a specific binding substance is readily affected by reaction of the conjugate with a specific binding counterpart of such specific binding substance. Examples of enzyme substrates which are contemplated for use in the present invention include the enzyme-cleavable fluorescent substrates referred to previously such as fluorescein and umbelliferone derivatives; pH indicators; and spectrophotometric indicator dyes, particularly chromogenic types.

For the above reasons and for reasons of versatility and adaptability, coenzymes are especially preferred for use as the reactant in the conjugate. A coenzyme is a non-protein molecule which migrates from one enzyme protein to another in facilitating the efficient performance of the catalytic function of the enzyme. All known coenzymes have a molecular weight of less than 9000, the preferred coenzymes having a molecular weight of less than about 5000. Useful coenzymes include the nucleotide coenzymes, particlarly those comprising adenine groups, such as the adenosine phosphates (i.e. the mono-, di-, and tri-phosphate forms), nicotinamide adenine dinucleotide and its reduced forms, and nicotinamide adenine dinucleotide phosphate and its reduced forms. Other useful coenzymes include the guanosine phosphates, flavin mononucleotide and its reduced forms, flavin adenine dinucleotide and its reduced forms, coenzyme A and its thioesters including succinyl-coenzyme A, 3', 5' adenosine diphosphate, and adenosine-3'-phosphate-5'-phosphosulfate.

Useful coenzyme-active conjugates comprise nucleotide coenzymes having an adenine group to which the specific binding substance, i.e., a ligand, a specific binding analog of a ligand, or a specific binding partner of a ligand, is coupled through a direct bond or a bridge group as referred to hereinbefore. Such coenzyme-active conjugates which comprise an adenosine phosphate, nicotinamide adenine dinucleotide or its reduced form, or nicotinamide adenine dinucleotide phosphate or its reduced form, have the following general formula:

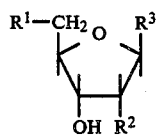

-continued

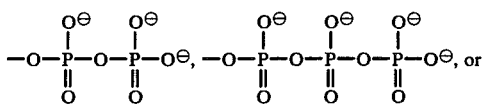

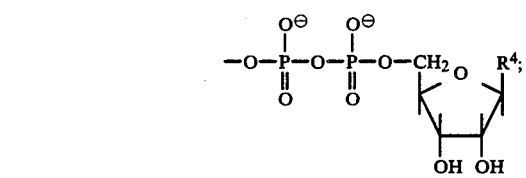

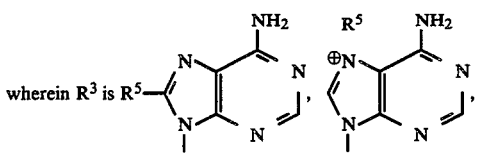

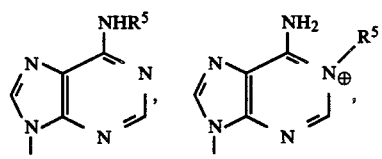

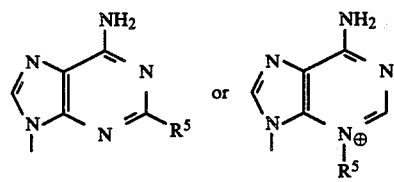

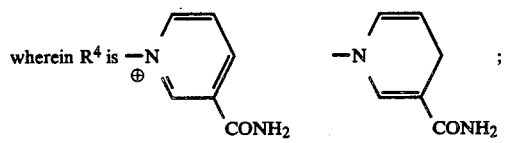

wherein $R^5$ is —Y—Z; wherein Y is a bond or a bridge group; and wherein Z is a ligand, a specific binding analog of a ligand, or a specific binding partner of a ligand. The above formula represents the ionized forms of the coenzyme-active conjugate, however, the protonized or acid forms are equally useful. The extent of protonization depends on the pH of the environment. Also, the salts of such conjugates may also be used where appropriate.

Synthesis of such compounds may be accomplished in a variety of ways. It is contemplated that the synthesis routes which are schematically illustrated below are advantageously followed in the preparation of the useful compounds. In the illustrated syntheses, the positions on the adenine ring structure are referred to according to the following:

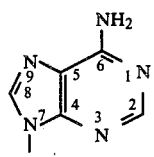

Also, the following abbreviations are used;

Rib refers to the ribose moiety, i.e., 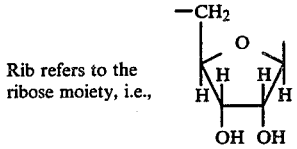

Rib' refers to the phosphated ribose moiety, i.e., 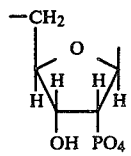

Ph refers to a phosphate group;

AP derivatives refers to derivatives of adenosine-5'-phosphate, i.e., the mono-(AMP), di-(ADP), or tri-(ATP) phosphate form;

NAD derivative refers to a derivative of either nicotinamide adenine dinucleotide or a reduced form thereof;

NADP derivative refers to a derivative of either nicotinamide adenine dinucleotide phosphate or a reduced form thereof;

R refers to the specific binding substance or a modification thereof; and

X refers to a leaving group, usually a halogen.

1-position derivatives of AP

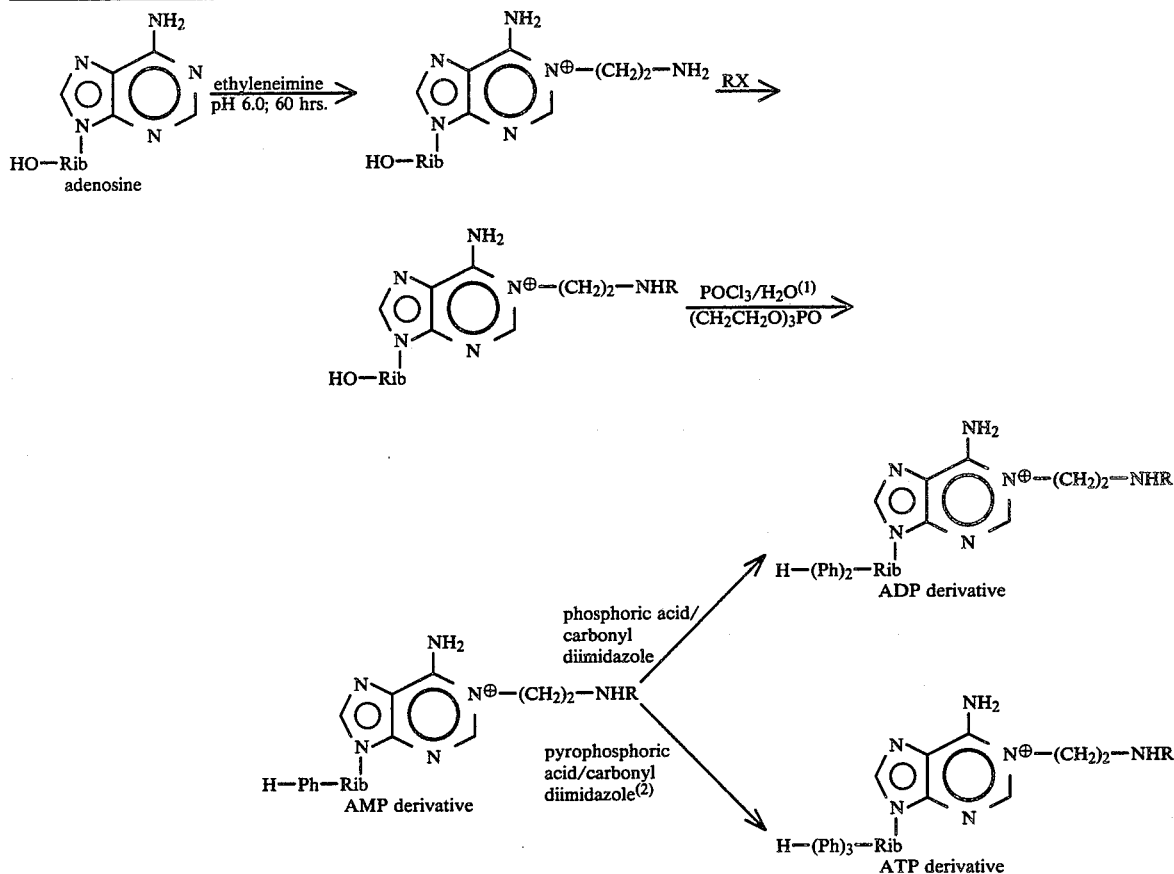

1-position derivative of NAD

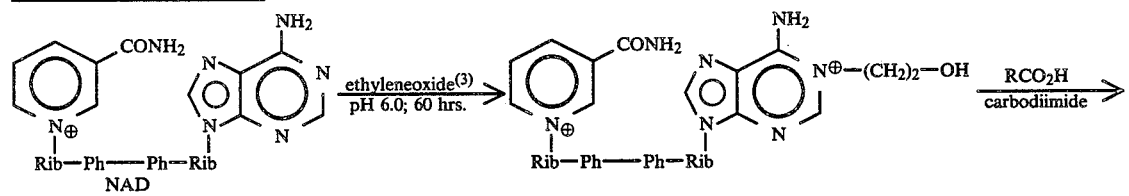

-continued
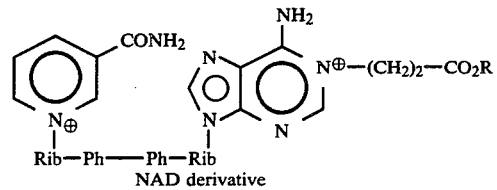
NAD derivative
1-position derivative of NADP
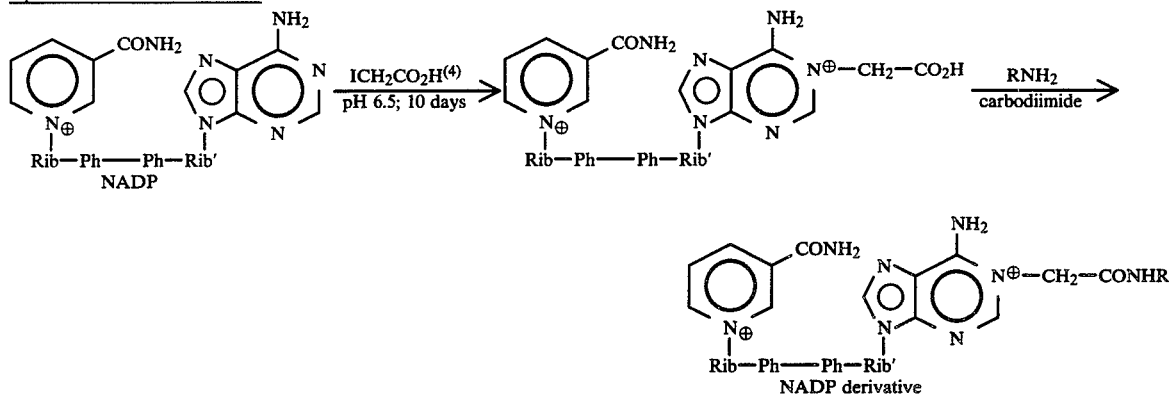
NADP derivative
2-position derivatives of AP
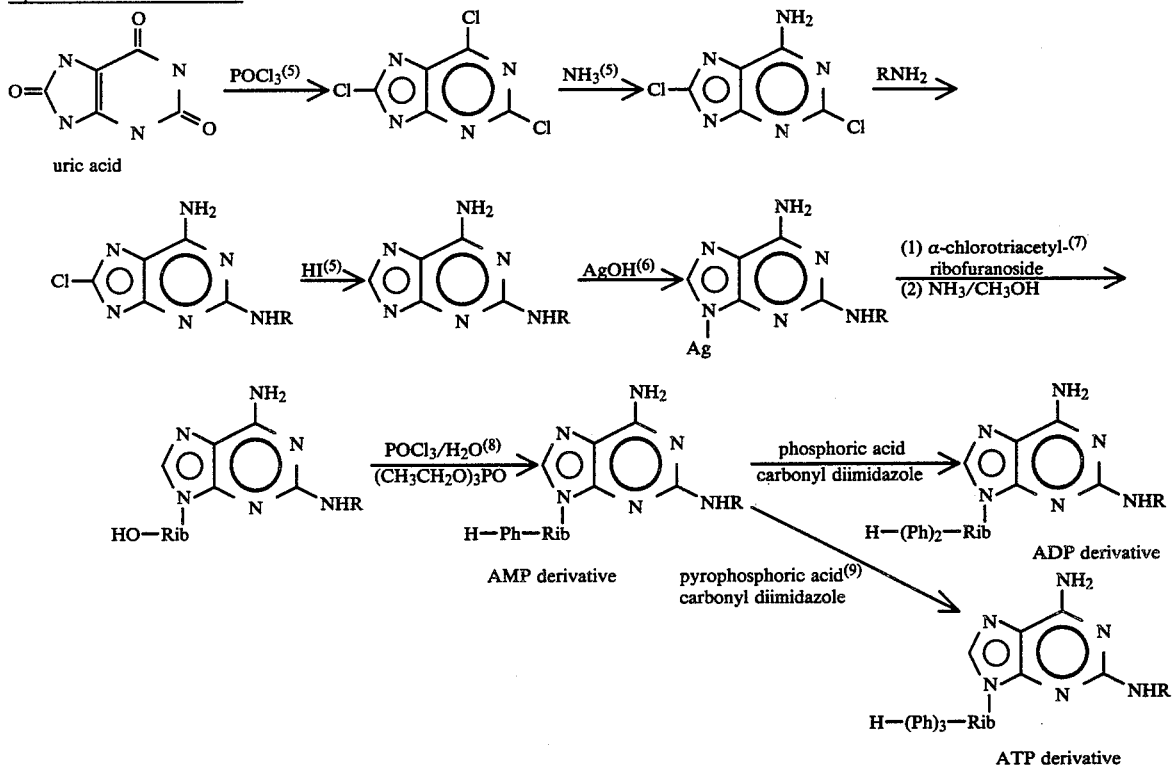
AMP derivative
ADP derivative
ATP derivative
2-position derivative of NAD
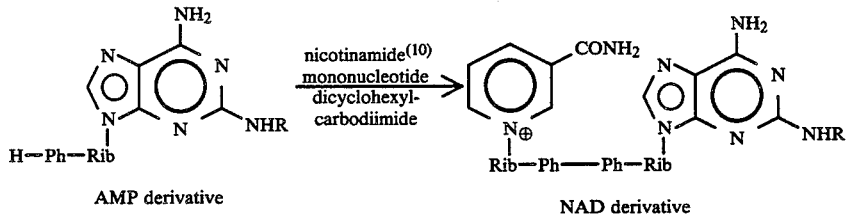
AMP derivative
NAD derivative
2-position derivative of NADP

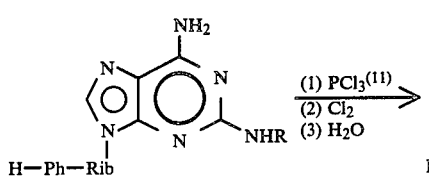
AMP derivative
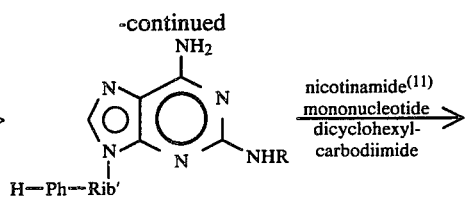
-continued
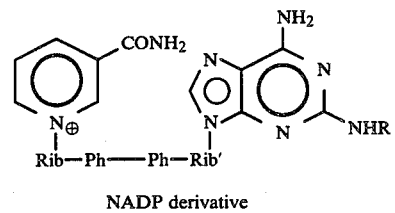
NADP derivative
3-position derivatives of AP
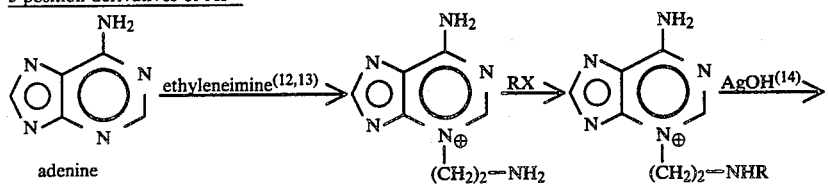
adenine
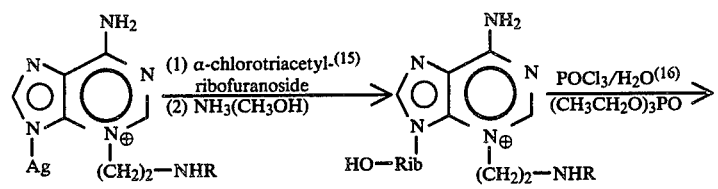
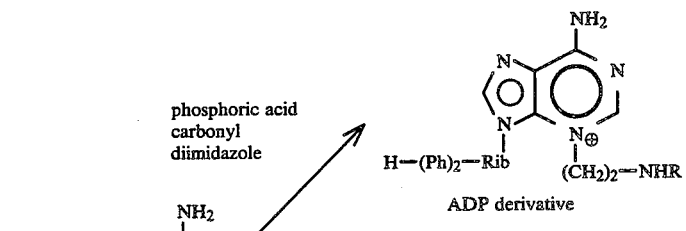
ADP derivative
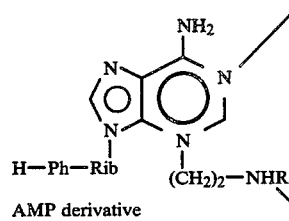
AMP derivative
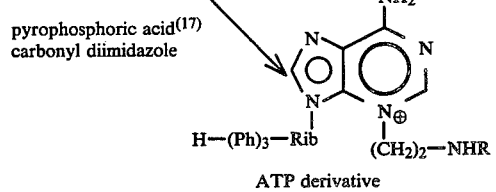
ATP derivative
3-position derivative of NAD
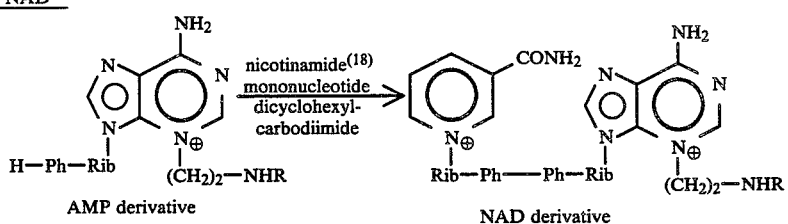
AMP derivative      NAD derivative -continued
3-position derivative of NADP
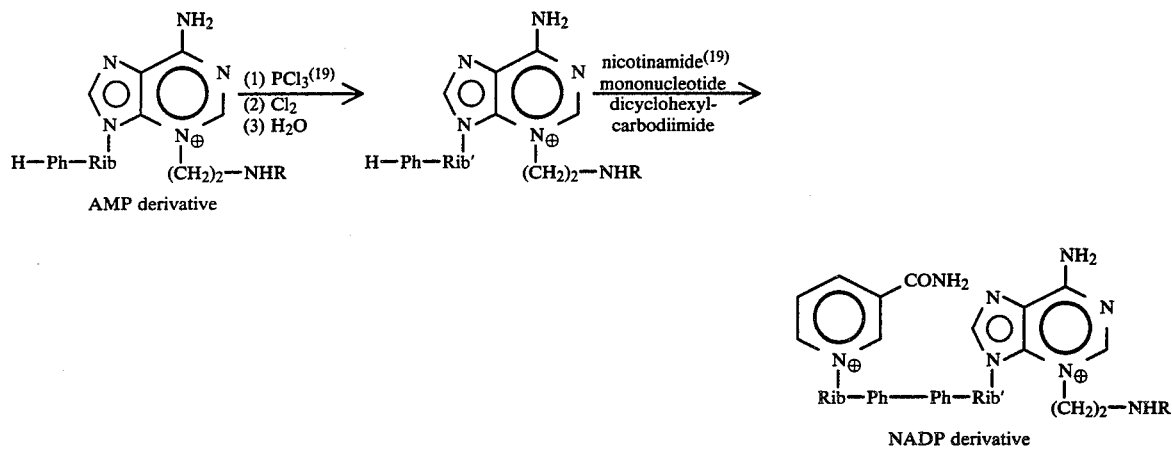
6-position derivatives of AP
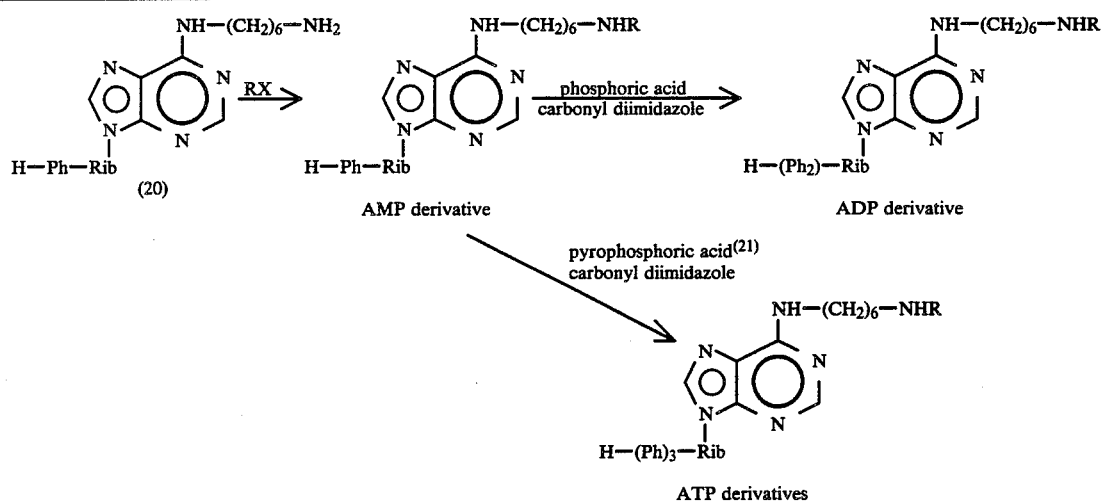
6-position derivative of NAD
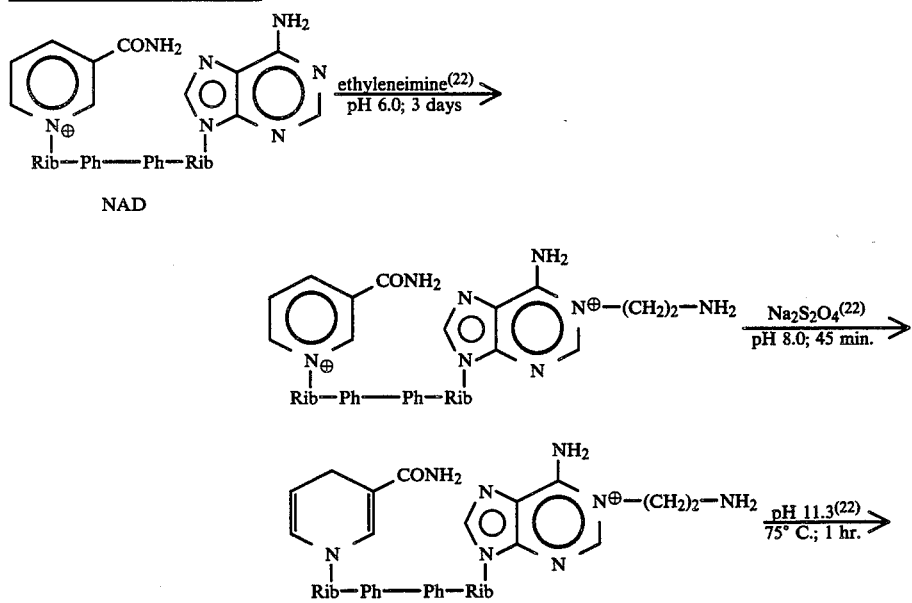

-continued
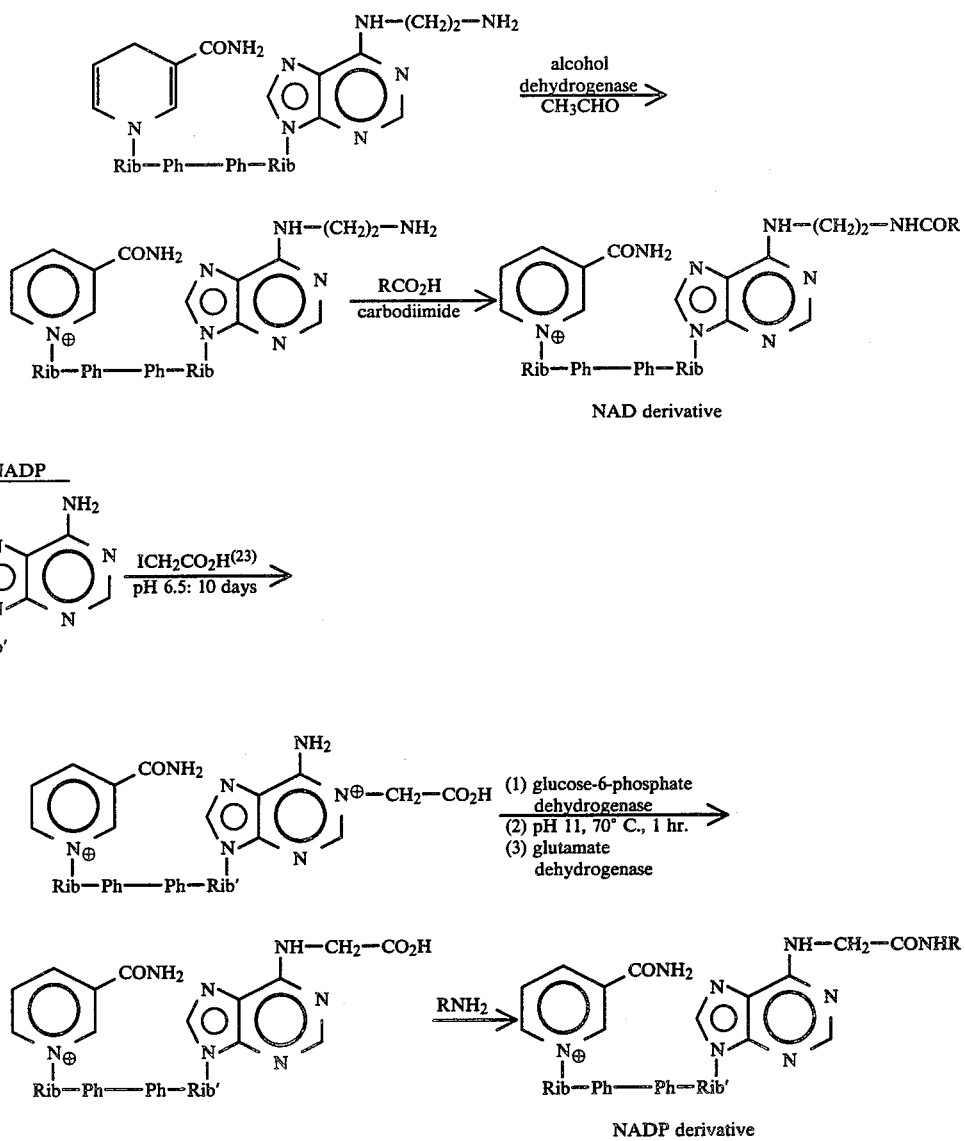
NAD derivative
6-position derivative of NADP
NADP
NADP derivative
8-position derivatives of AP
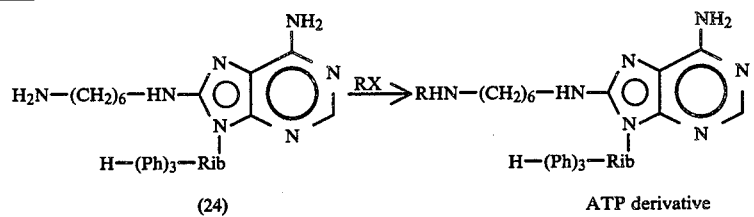
(24)    ATP derivative
8-position derivative of NAD
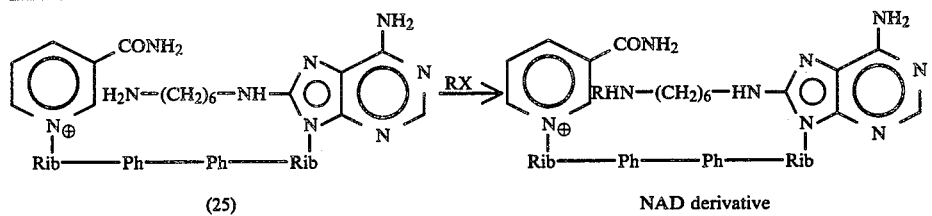
(25)    NAD derivative
8-position derivative of NADP

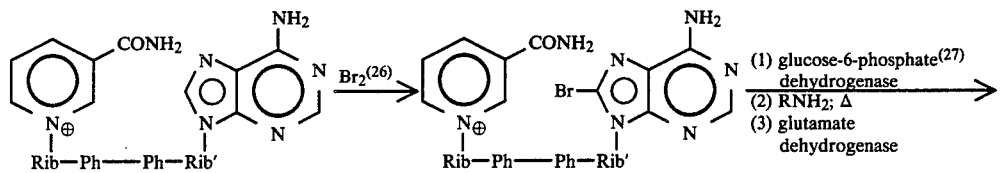
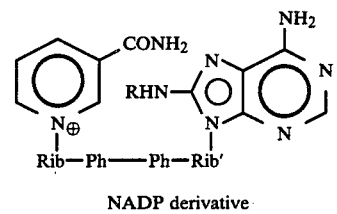
NADP derivative
9-position derivatives of AP
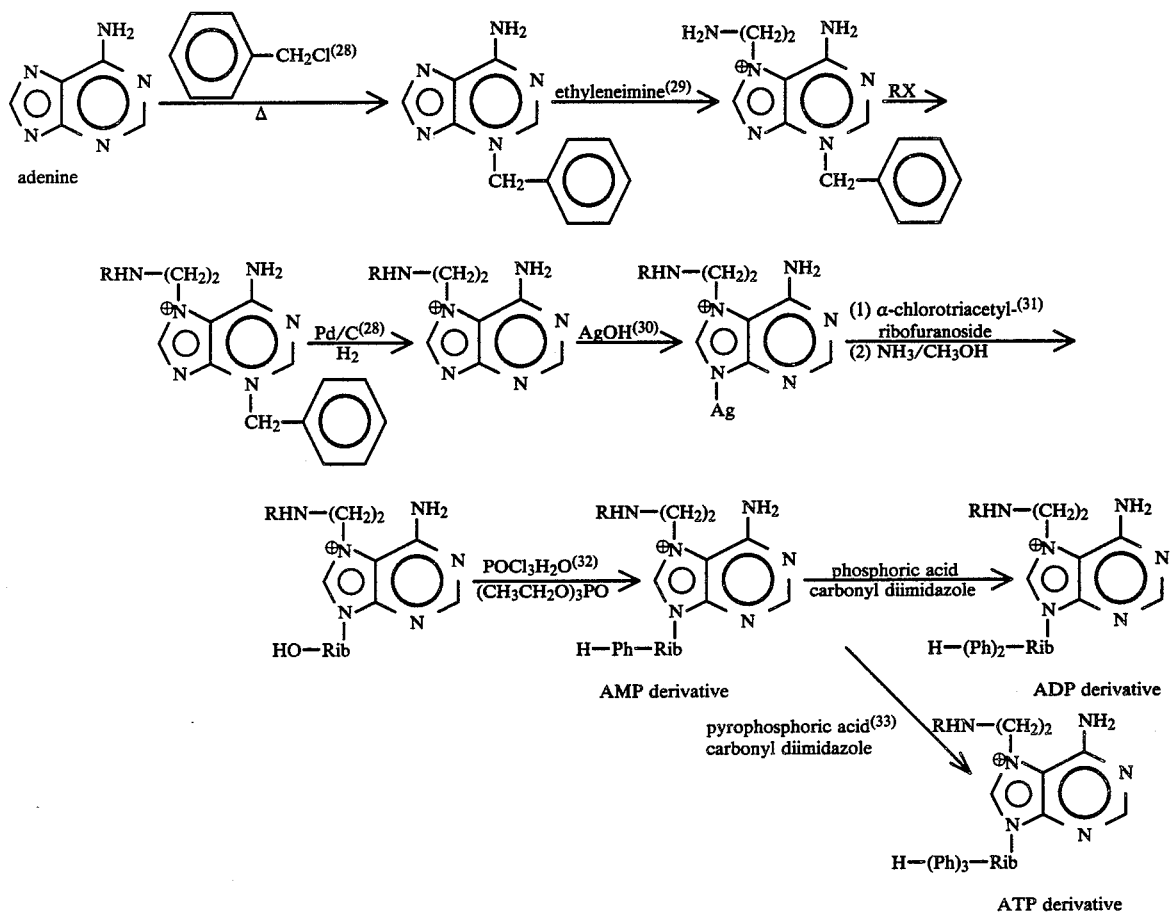
9-position derivative of NAD
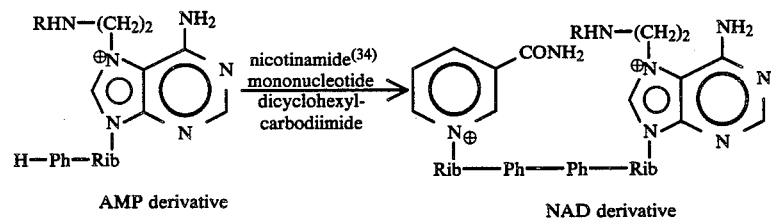
9-position derivative of NADP -continued

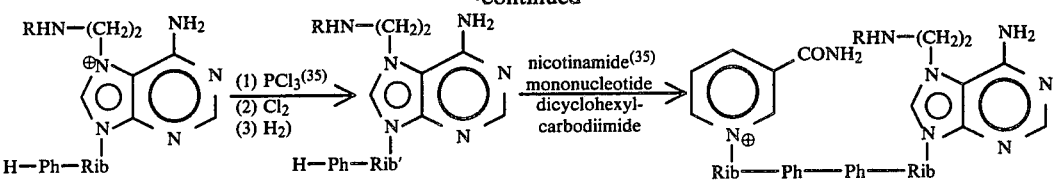

AMP derivative                                           NADP derivative

[1] Guilford, H., et al., Chemica Scripta 2:165 (1972).
[2] Trayer, I. P., et al., Biochem. J. 139:609 (1974).
[3] Windmueller, H. G., and Kaplan, N. O., J. Biol Chem. 236:2716 (1961).
[4] Lowe, C. R. and Mosbach, K., Eur. J. Biochem. 49:511 (1974).
[5] Acheson, R. M., An Introduction to the Chemistry of Heterocyclic Compounds. Interscience Publ. (New York 1962), p. 308.
[6] Fischer, E., Ber. 30:2239 (1897).
[7] Davoll et al., J. Chem. Soc., 967 (1948).
[8] Guilford, H., et al., supra.
[9] Trayer, I. P., et al., supra.
[10] Hughes, N. A., et al., J. Chem. Soc., 3733 (1957).
[11] Hughes, N. A., et al., supra.
[12] Lister, J. H., in Advances in Heterocyclic Chemistry, ed. Kabritzky et al., Academic Press (New York, 1966), p. 33.
[13] Leonard, N. J., and Fujii, T. J., J. Amer. Chem. Soc. 85:3719 (1963).
[14] Fischer, E., supra.
[15] Davoll et al., supra.
[16] Guilford, H., et al., supra.
[17] Trayer, I. P., et al., supra.
[18] Hughes, N. A., et al. supra.
[19] Hughes, N. A., et al., supra.
[20] Guilford, H., et al., supra.
[21] Trayer, I. P., et al., supra.
[22] Windmueller, H. G., and Kaplan, N. O., J. Biol. Chem. 236:2716 (1961).
[23] Lowe, C. R., and Mosbach, K., supra.
[24] Trayer, I. P., et al., supra.
[25] Lee, C-Y, et al., Arch. Biochem. Biophys. 163:561 (1974).
[26] Lee, C-Y, et al., supra.
[27] Lowe, C. R. and Mosbach, R., supra.
[28] Leonard, N. J., and Fujii, T. J., supra.
[29] Lister, J. H., supra.
[30] Fischer, E., supra.
[31] Davoll, et al., supra.
[32] Guildford, H., et al., supra.
[33] Trayer, I. P., et al., supra.
[34] Hughes, N. A., et al., supra.
[35] Hughes, N. A., et al., supra.

In addition to the compounds mentioned above, useful enzyme-active conjugates include the adenosine phosphates to which are coupled to specific binding substance through the phosphate grouping. Such compounds have the following general formula:

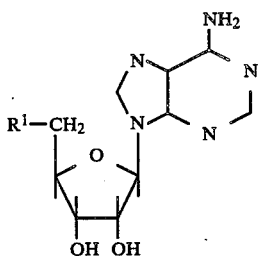

wherein $R^1$ is

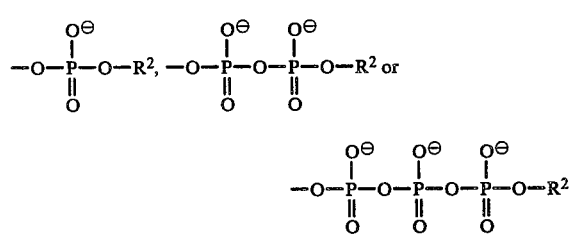

wherein $R^2$ is —Y—Z; wherein Y is a bond or a bridge group; and wherein Z is a ligand, a specific binding analog of a ligand, or a specific binding partner of a ligand. Also, the protonized or acid forms, as well as the salt forms where appropriate, may be used.

Synthesis of such compounds may be accomplished in a variety of ways. It is contemplated that the synthesis routes which are schematically illustrated below are advantageously followed in the preparation of the useful compounds. The abbreviations used hereinbefore also apply to the illustration to follow.

derivatives of AP

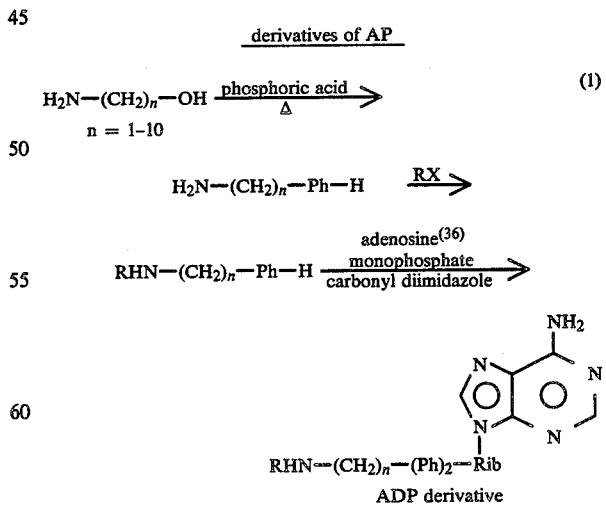

ADP derivative

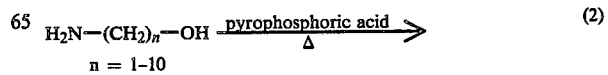

33
-continued
derivatives of AP

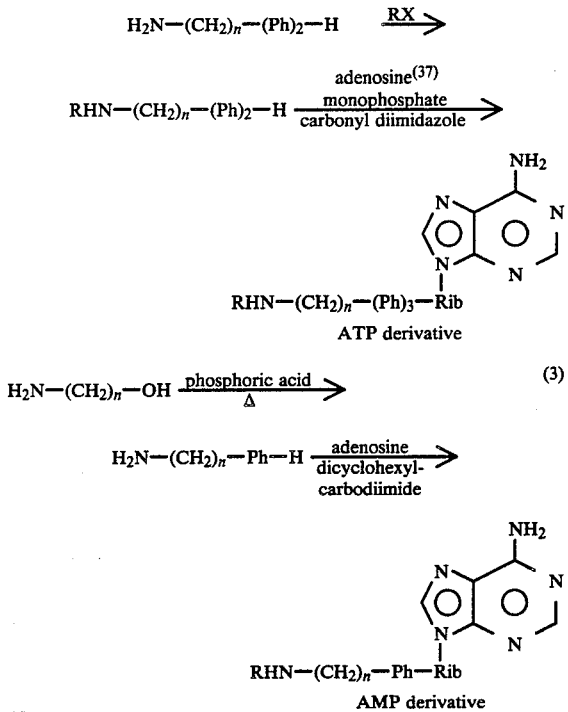

(36) Trayer, I. P., et al., Biochem. J. 139:609 (1974).
(37) Trayer, I. P., et al., supra.

In one form of the present invention, the components of the specific binding reaction which are to be combined with the liquid medium suspected of containing the ligand are in a liquid or solid form. In the preferred homogeneous assay system, the components are usually in solution or in a solid form capable of ready dissolution in the liquid medium. Since the liquid medium to be tested is normally aqueous in character, the components are generally in a water soluble form, that is, either in aqueous solution or in a water soluble solid form such as a powder or resin. The assay method may be carried out in a standard laboratory vessel such as a test tube with the specific binding reaction components and the components of the reaction system being added thereto in solid or liquid form.

It is also contemplated that one or more of the specific binding reaction components and/or one or more of the components of the monitoring reaction may be incorporated with a carrier. In one aspect, the carrier may be a liquid-holding vessel such as a test tube or capsule containing such component or components in an interior portion thereof, for instance, in the form of a liquid or loose solid or a coating on an interior surface of the vessel. In another aspect, the carrier may be in the form of matrix which is insoluble and porous, and preferably absorbent, relative to the liquid medium to be tested. Such matrix may be in the form of bibulous papers; polymeric films, membranes, fleeces, or blocks; gels; and so forth. In such a form, the device would provide a convenient means for contacting the liquid medium to be tested, for carrying out the specific binding reaction and/or the monitoring reaction, and for observing the resulting response.

The liquid medium to be tested may be a naturally occurring or artificially formed liquid suspected of containing the ligand, and usually is a biological fluid or a liquid resulting from a dilution or other treatment thereof. Biological fluids which may be assayed following the present method include serum, plasma, urine, and amniotic, cerebral, and spinal fluids. Other materials such as solid matter, for example tissue, or gases may be assayed by reducing them to a liquid form such as by dissolution of the solid or gas in a liquid or by liquid extraction of the solid.

In contrast to the prior art homogeneous assay system, biological fluids containing substances which have reactant activity similar or identical to that of the conjugated labeling substance may be assayed for the ligand without background interference. Endogenous background reactant activity can be readily eliminated in several manners. The biological fluid can be treated to selectively destroy the endogenous reactant activity. Such treatment may involve the action of a clearing agent which chemically destroys the endogenous activity followed by treatment to inactivate the destructive action of such clearing agent.

For instance, reactant-degrading enzymes often appear naturally in biological fluids, particularly if the reactant is a coenzyme such as NAD, NADP, or ATP. There are many inhibitors of such coenzyme-degrading enzymes, for example, chelating agents which operate to deprive the enzymes of essential metal ion activators. As a specific example, NAD-degrading enzymes are found in normal serum and have sufficient enzymatic activity to remove essentially all endogenous NAD activity from isolated serum within a few hours. The degrading activity of such enzymes may be effectively inhibited by addition of a chelating agent such as ethylenediamine tetraacetic acid. Elimination of the degrading activity may also be accomplished by adding a specific enzyme inhibitor. For example, ATP-degrading enzymes may be inhibited by addition of $\beta\gamma$ methylene ATP or $\alpha\beta$ methylene ATP.

The present invention will now be illustrated, but is not intended to be limited, by the following Examples.

EXAMPLE 1

Preparation of nicotinamide 6-(2-aminoethylamino)-purine dinucleotide.

Two (2) grams of nicotinamide adenine dinucleotide (NAD) were dissolved in 10 ml of water and 0.6 ml of ethyleneimine was added dropwise, the pH being maintained below 7 by the addition of 1M perchloric acid. When addition of ethyleneimine was complete, the pH was adjusted to 4.5 and the reaction was incubated at 20°–25° C. At 24 hour intervals 0.6 ml of ethyleneimine was added and the pH readjusted to 4.5. After 96 hours, the solution was poured into 10 volumes of acetone at −10° C. The oil which formed was collected, washed with ether, and dissolved in approximately 50 ml of water in a flask.

The resulting solution was adjusted to pH 7.0–7.5 with 1N sodium hydroxide, and 1 gram of sodium bicarbonate was added. Nitrogen was bubbled through the solution for from 4 to 5 minutes and 1 gram of sodium hydrosulfite was added. The flask was sealed tightly and allowed to stand at room temperature for 45 minutes. The solution was then oxygenated for 15 minutes and adjusted to pH 11.3 with sodium hydroxide. The solution was heated at 75° C. for 1 hour. Then the reaction mixture was cooled to room temperature and 0.6 grams of tris-(hydroxymethyl)-aminomethane was added, followed by 5N hydrochloric acid to adjust the pH to 7.5. To the resulting solution was added 1000 International units of alcohol dehydrogenase and 1 ml of acetaldehyde. The decreasing optical density of the reaction mixture was monitored at 340 nm and when no further decrease was observed, the pH was adjusted to 3.5. The solution was poured into 10 volumes of acetone at −10° C. The oil which formed was separated and washed with ether, after which it was dissolved in 10 to 15 ml of water.

The resulting solution was introduced into a 2.5×90 cm column of Sephadex G-10, available from Pharmacia AB, Uppsala, Sweden, equilabrated with water. Fractions of 12 ml volume were collected. The wavelength of maximum optical absorption in the ultraviolet region and the optical density at such wavelength were determined for each fraction. Also, the optical density at 340 nm of each fraction after reduction with alcohol dehydrogenase was determined. The fractions which had an optical absorption maximum at 264 nm and had a ratio of optical density at 340 nm to that at 264 nm greater than 0.05 were pooled. The pooled material was concentrated to from 15 to 20 ml on a rotary evaporator and passed through a 2.5×28 cm column of Dowex 1-X8, available from Bio-Rad Laboratories, Richmond, Calif., equilabrated with water. Additional water was added to wash the pooled material through the column, and 10 ml fractions were collected. The fractions which had an optical absorption maximum at 264 nm and had a ratio of optical density at 340 nm to that at 264 nm greater than 0.1 were pooled.

The pooled material was passed through a 5×45 cm column of Dowex 50-X2, available from Bio-Rad Laboratories, Richmond, Calif., equilibrated with water. Additional water was added to wash the pooled material through the column and 20 ml fractions were collected. The fractions which had an optical absorption maximum at 264 nm and had a ratio of optical density at 340 nm to that at 264 g greater than 0.18 were pooled. The pooled material was concentrated to from 4 to 5 ml and purified by electrophoresis as follows.

The concentrated material was applied to a sheet of Whatman 3MM paper, available from Reeve Angel, Clifton, N.J., in a 1 to 2 cm wide strip perpendicular to the direction of current flow. The paper was then wetted with 0.02M sodium phosphate at pH 6.0. Electrophoresis was conducted according to the Durrum hanging paper method, as described in *Science* 121: 829 (1955), for 4-7 hours with a potential gradient of about 8.5 volts/cm. The location of the desired pyridine nucleotide derivative was determined by fluorescence developed after spraying a test strip of the paper with 0.5M sodium cyanide according to the procedure described in *J. Biol. Chem.* 191: 447 (1951). The area containing the desired derivative was cut out of the paper and extracted with three (3) 50 ml volumes of water. The resulting extracts containing nicotinamide 6-(2-aminoethylamino)purine dinucleotide were pooled, concentrated to from 3 to 4 ml, and stored at −20° C.

EXAMPLE 2

Preparation of nicotinamide adenine dinucleotide-biotin conjugate.

A 16 mg quantity of biotin was suspended in 1 ml of water containing 22 mg of nicotinamide 6-(2-aminoethylamino)purine dinucleotide prepared as in Example 1. A few drops of 0.1N sodium hydroxide was added to aid dissolution of the biotin. A 240 mg quantity of 1-cyclohexyl-3-(2-morpholinoethyl)-carbodiimide metho-p-tolulene sulfonate was added to the resulting solution and brought into solution by dropwise addition of 0.1N hydrochloric acid. The reaction mixture was allowed to incubate at room temperature for 5 hours and was then poured into 10 ml of acetone at −10° C. The oil which formed was separated, washed twice with from 5 to 10 ml of ether and dissolved in from 1 to 2 ml of water. The resulting material was purified by electrophoresis on paper as in Example 1. Two fluorescent bands appeared after spraying with sodium cyanide, one having migrated toward the cathode and the other toward the anode. The latter band, which contained the NAD-biotin conjugate, was eluted with water and stored at −20° C.

EXAMPLE 3

Preparation of nicotinamide adenine dinucleotide-2,4 dinitrophenyl conjugate.

A 26 mg quantity of sodium bicarbonate was dissolved in 1.5 ml of water containing 23 mg of nicotinamide 6-(2-aminoethylamino)purine dinucleotide prepared as in Example 1. To the resulting solution was added 3 ml of ethanol containing 17 μl of 2,4 dinitrofluorobenzene. The reaction mixture was stirred at room temperature in the dark for 5 hours after which 45 ml of acetone at −10° C. was added thereto. The precipitate which formed was separated, washed twice with 10 ml of acetone, and stirred with 5 ml of water. The yellow soluble material which separated was purified by electrophoresis on paper as in Example 1 for 5 hours. The band which migrated toward the anode, and which contained the NAD-2,4 dinitrophenyl conjugate, was eluted with water, concentrated to from 3 to 5 ml, and stored at −20° C.

EXAMPLE 4

Preparation of biotin-umbelliferone conjugate.

A reaction mixture was formed by dissolving in 10 ml of dimethylformamide 100 mg of umbelliferone, 167 mg of biotin, and 141 mg of dicyclohexyl carbodiimide. The reaction mixture was incubated at −18° C. for about 4 hours, then overnight at 7° C. and allowed to stand at room temperature for from 3 to 4 hours. An additional 141 mg of dicyclohexylcarbodiimide was added and the reaction mixture was stirred at 7° C. for from 3 to 4 hours and allowed to stand at room temperature overnight. The resulting precipitate was filtered off and discarded. To the filtrate was added 75 ml of ice water, and the resulting mixture was incubated at 0° C. for 1 hour. The precipitate which resulted was filtered off and discarded. The filtrate was evaporated to dryness and the residue dissolved in from 3 to 4 ml of methylene chloride. To the resulting solution was added 5 ml of diethylether. The resulting precipitate which comprised the biotin-umbelligerone conjugate was filtered off, dried, and stored at room temperature.

EXAMPLE 5

Effect of avidin and biotin on the enzymatic cycling rate of NAD and NAD-biotin conjugates.

The cycling reaction system used in this Example was based on the following reactions:

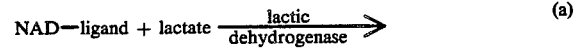

-continued

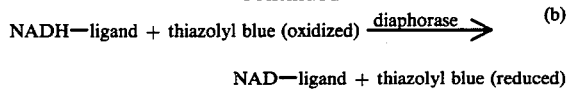

Eight specific binding reaction mixtures were prepared, each having a total volume of 0.5 ml and containing 0.12M N,N bis-2-hydroxyethylglycine hydrochloride buffer at pH 7.8 and respectively containing the concentrations and activities indicated in Table 1 of NAD, NAD-biotin conjugate prepared as in Example 2, biotin, and avidin, which latter has an affinity for binding with biotin. One (1) unit of avidin activity is that quantity of avidin capable of binding 1 μg of biotin. The reaction mixtures were incubated at room temperature for from 2 to 3 hours. Each reaction mixture was contacted with an aqueous enzyme/substrate mixture by the addition of 0.1 ml of 1M lithium lactate, 0.05 ml of 10 mM thiazolyl blue in its oxidized form, and a sufficient quantity of 0.12M N,N bis-2-hydroxyethylglycine hydrochloride buffer at pH 7.8 containing 0.38 International units of bovine heart lactic dehydrogenase, and 1.5 International units of porcine heart diaphorase to give a total reaction volume of 1 ml. The relative rate of production of the reduced form of thiazolyl blue was then determined in each of the reaction mixtures by measuring the total change in the optical density in each thereof at 570 nm during a 24 minute period within the first hour after the addition of the enzyme/substrate mixture. The entire procedure was performed in duplicate and the averaged results appear in Table 1.

The cycling reaction system used in this Example was the same as that diagrammed in Example 5. Seven specific binding reaction mixtures were prepared, each having a total volume of 0.6 ml and each containing 0.12M N,N bis-2-hydroxyethylglycine hydrochloride buffer at pH 7.8 and 250 nM NAD-biotin conjugate prepared as in Example 2. Six of the reaction mixtures also contained avidin in the amounts indicated in Table 2.

The reaction mixtures were incubated at room temperature for from 2 to 3 hours. Each reaction mixture was contacted with an aqueous enzyme/substrate mixture by the addition of 0.1 ml of 1M lithium lactate, 0.05 ml of 10 mM thiazolyl blue in its oxidized form, and a sufficient quantity of 0.12M N,N bis-2-hydroxyethylglycine hydrochloride buffer at pH 7.8 containing 0.38 International units of bovine heart lactic dehydrogenase and 1.5 International units of porcine heart diaphorase to give a total reaction volume of 1 ml. The relative rate of production of the reduced form of thiazolyl blue was then determined in each of the reaction mixtures by measuring the total change in the optical density in each thereof at 570 nm during a 24 minute period within the first hour after the addition of the enzyme/substrate mixture. The ratio, expressed as percent, of the change in optical density in each reaction mixture containing avidin to that in the reaction mixture not containing avidin was calculated and is referred to in Table 2 and FIG. 1 as the relative cycling rate. The results appear in Table 2 and in graphical form in FIG. 1 of the drawing.

TABLE 1

| reaction | concentration of NAD (nM) | concentration of NAD-biotin conjugate (nM) | concentration of biotin (nM) | avidin activity (units) | average increase in optical density (570 nm) |
|---|---|---|---|---|---|
| 1 | — | — | — | — | 0.002 |
| 2 | 220 | — | — | — | 0.103 |
| 3 | — | 360 | — | — | 0.079 |
| 4 | — | — | 360 | — | 0.003 |
| 5 | 220 | — | — | 0.11 | 0.103 |
| 6 | — | 360 | — | 0.11 | 0.025 |
| 7 | — | 360 | 360 | 0.11 | 0.069 |
| 8 | — | — | — | 0.11 | 0.001 |

Reactions 1, 4, and 8 were controls and show that in the absence of NAD and the NAD-biotin conjugate essentially no cycling occurred. The results of reactions 2 and 3 demonstrate that the NAD-biotin conjugate has a significant amount of coenzyme activity relative to native NAD. It can be seen from the results of reactions 3 and 6 that the presence of avidin in the reaction mixture inhibits the formation of thiazolyl blue (reduced form) where the NAD present is conjugated with biotin. By comparing the results of reactions 6 and 7 it can be seen that the presence of free biotin reduces the amount of inhibition of thiazolyl blue (reduced form) formation in proportion to the concentration of biotin in the reaction mixture.

It was thus demonstrated in this Example that the activity of the NAD in the NAD-biotin conjugate relative to the cycling reaction system was decreased in the presence of avidin and that the magnitude of such decrease in activity was reduced by the additional presence of biotin.

EXAMPLE 6

Direct binding-cycling assay for avidin; effect of varying levels of avidin on the cycling rate.

TABLE 2

| reaction mixture | amount of avidin added (units) | relative cycling rate (%) |
|---|---|---|
| 1 | 0.000 | 100 |
| 2 | 0.005 | 96 |
| 3 | 0.010 | 93 |
| 4 | 0.045 | 84 |
| 5 | 0.090 | 68 |
| 6 | 0.120 | 51 |
| 7 | 0.180 | 8 |

It was demonstrated in this Example that the relative cycling rate of the cycling reaction system, and thus the activity of the NAD in the NAD-biotin conjugate, was an inverse function of the amount of avidin present in the specific binding reaction mixture. The present invention therefore provides a test composition and method for quantitatively determining the presence of the ligand avidin in a liquid medium using a direct binding-cycling assay technique.

EXAMPLE 7

Competitive binding-cycling assay for biotin; effect of varying levels of biotin on the cycling rate.

The cycling reaction system used in this Example was the same as that diagrammed in Example 5. Seven specific binding reaction mixtures were prepared, each having a total volume of 0.45 ml and each containing 0.12M N,N bis-2-hydroxyethylglycine hydrochloride buffer at pH 7.8 and 180 nM NAD-biotin conjugate prepared as in Example 2. Six of the reaction mixtures, i.e. nos. 1 through 6 in Table 3, additionally contained 0.11 units of avidin. Also, biotin, at the concentrations indicated in Table 3, was included in five of the six reaction mixtures containing avidin, i.e. mixtures 2 through 6 in Table 3.

Figure 2:
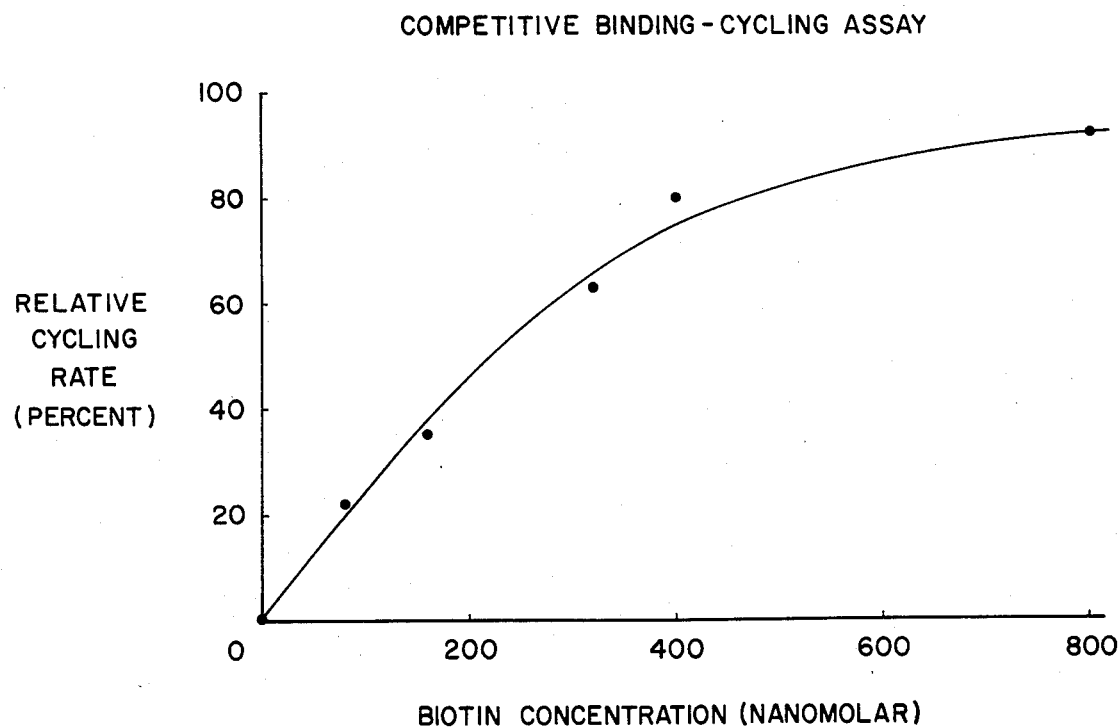
FIGS. 2 and 3, respectively, are graphical representations of the effect of various levels of two different ligands on the aggregate reaction rate in a competitive binding-cycling assay technique.

The reaction mixtures were incubated at room temperature for from 2 to 3 hours. Each reaction mixture was contacted with an aqueous enzyme/substrate mixture by the addition of 0.1 ml of 1M lithium lactate, 0.05 ml of 10 mM thiazolyl blue in its oxidized form and a sufficient quantity of 0.12M N,N bis-2-hydroxyethylglycine hydrochloride buffer at pH 7.8 containing 0.38 International units of bovine heart lactic dehydrogenase and 1.5 International units of porcine heart diaphorase to give a total reaction volume of 1 ml. The relative rate of production of the reduced form of thiazolyl blue was then determined in each of the reaction mixtures by measuring the total change in the optical density in each thereof at 570 nm during a 24 minute period within the first hour after the addition of the enzyme/substrate mixture. The ratio, expressed as percent, of such change in optical density in each reaction mixture containing biotin to that in the reaction mixture not containing either biotin or avidin was calculated and is referred to in Table 3 and FIG. 2 as the relative cycling rate. The results appear in Table 3 and in graphical form in FIG. 2 of the drawing.

TABLE 3

| reaction mixture | concentration of biotin (nM) | relative cycling rate (%) |
|---|---|---|
| 1 | 0 | 8 |
| 2 | 80 | 22 |
| 3 | 160 | 35 |
| 4 | 320 | 63 |
| 5 | 400 | 80 |
| 6 | 800 | 92 |

It was demonstrated in this Example that the relative cycling rate of the cycling reaction system, and thus the activity of the NAD in the NAD-biotin conjugate, was a direct function of the amount of biotin present in the specific binding reaction mixture. The present invention therefore provides a test composition and method for quantitatively determining the presence of the ligand biotin in a liquid medium using a competitive binding-cycling assay technique.

EXAMPLE 8

Direct binding-cycling assay for antibody to 2,4 dinitrophenyl and derivatives thereof.

The cycling reaction system used in this Example was the same as that described in Example 5. Eight 0.6 ml specific binding reaction mixtures were prepared, each containing 0.12M N,N bis-hydroxyethylglycine hydrochloride buffer at pH 7.8 and respectively containing the amounts and concentrations indicated in Table 4 of NAD, NAD-2,4 dinitrophenyl conjugate prepared as in Example 3, antiserum to 2,4 dinitrophenyl, and nicotinamide mononucleotide (NMN). The reaction mixtures were incubated at room temperature for from 3 to 4 hours. Each reaction mixture was contacted with an aqueous enzyme/substrate mixture by the addition of 0.1 ml of 1M lithium lactate, 0.05 ml of 10 mM thiazolyl blue in its oxidized form, and a sufficient quantity of 0.12M N,N bis-hydroxyethylglycine hydrochloride buffer at pH 7.8 containing 0.38 International units of bovine heart lactic dehydrogenase and 1.5 International units of porcine heart diaphorase to give a total reaction volume of 1 ml. The relative rate of production of the reduced form of thiazolyl blue was determined in each of the reaction mixtures by measuring the total change in the optical density in each thereof at 570 nm during a 24 minute period within the first hour after the addition of the enzyme/substrate mixture. The entire procedure was performed in duplicate and the averaged results appear in Table 4.

TABLE 4

| reaction | concentration of NAD ($\mu$M) | concentration of NAD-2,4 dinitrophenyl conjugate (nM) | concentration of NMN ($\mu$M) | amount of antiserum ($\mu$l) | average increase in optical density (570 nm) |
|---|---|---|---|---|---|
| 1 | — | — | — | — | 0.005 |
| 2 | — | 290 | — | — | 0.164 |
| 3 | 1.75 | — | — | — | 0.608 |
| 4 | 1.75 | — | 50 | — | 0.699 |
| 5 | 1.75 | — | — | 100 | 0.275 |
| 6 | 1.75 | — | 50 | 100 | 0.648 |
| 7 | — | 290 | — | 100 | 0.021 |
| 8 | — | 290 | 50 | 100 | 0.037 |

Reaction 1 was a control and shows that in the absence of NAD and the NAD-2,4 dinitrophenyl conjugate essentially no cycling occurred. From the results of reaction 2 it is demonstrated that the NAD-2,4 dinitrophenyl conjugate is active in the enzymatic cycling system. The results of reactions 3 and 5 indicate that the presence of antibody to 2,4 dinitrophenyl inhibits the cycling of NAD. As shown by the results of reaction 6, such inhibition is reversed by addition of NMN. From the results of reactions 3 and 4 it is seen that the cycling rate in the presence of NMN is about 15% greater than in its absence. This result is probably due to contamination by extraneous NAD because other measurements have shown that NMN does not influence the cycling rate in the absence of antibody. Nevertheless, the antiserum contains some activity with respect to NAD itself which activity is inhibited by the presence of NMN.

It was thus demonstrated in this Example that the activity of the NAD in the NAD-2,4 dinitrophenyl conjugate relative to the cycling reaction system was decreased in the presence of antibody to 2,4 dinitrophenyl. The present invention therefore provides a test composition and method for determining the presence of the ligand antibody to 2,4 dinitrophenyl in a liquid medium using a direct binding-cycling assay technique.

EXAMPLE 9

Competitive binding-cycling assay for 2,4-dinitrobenzene and derivatives thereof; effect of various levels of N (2,4 dinitrophenyl)-6-aminocaproate on the cycling rate.

The cycling reaction system used in this Example was the same as that diagrammed in Example 5. Seven specific binding reaction mixtures were prepared, each having a total volume of 0.6 ml and each containing 0.12M N,N bis-hydroxyethylglycine hydrochloride buffer at pH 7.8, 300 nM NAD-dinitrophenyl conjugate prepared as in Example 3, and 50 μM nicotinamide mononucleotide. Six of the seven reaction mixtures, i.e. nos. 1 through 6 in Table 5, also contained an amount of antibody to 2,4 dinitrophenyl sufficient to inhibit the cycling rate of the other reaction mixture by 85 percent. N (2,4 dinitrophenyl)-6-aminocaproate, a derivative of 2,4 dinitrobenzene prepared by the method described in Biochem. J. 42: 287 (1948), was also included in five of the six antibody-containing reaction mixtures, i.e. nos. 2 through 6 in Table 5, at the concentrations indicated in said Table.

Figure 3:
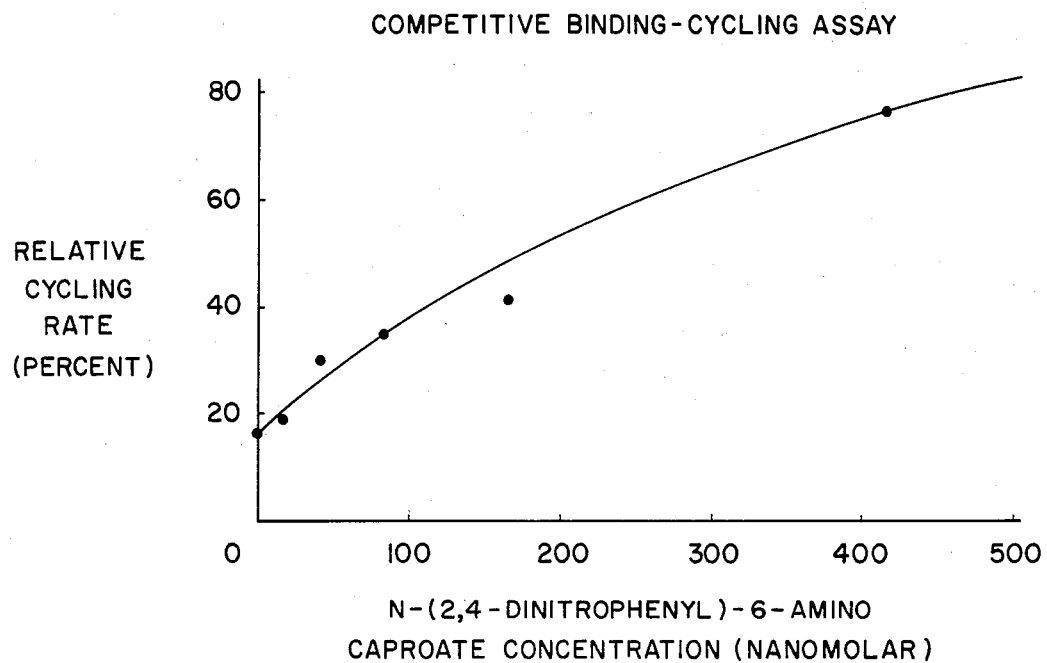

The reaction mixtures were incubated at room temperature for about 4 hours. Each reaction mixture was contacted with an aqueous enzyme/substrate mixture by the addition of 0.1 ml of 1M lithium lactate, 0.05 ml of 10 mM thiazolyl blue in its oxidized form, and a sufficient quantity of 0.12M N,N bis-hydroxyethylglycine hydrochloride buffer at pH 7.8 containing 0.38 International units of bovine heart lactic dehydrogenase and 1.5 International units of porcine heart diaphorase to give a total reaction volume of 1 ml. The relative rate of production of the reduced form of thiazolyl blue was determined in each of the reaction mixtures by measuring the total change in the optical density in each thereof at 570 nm during a 24 minute period within the first hour after the addition of the enzyme/substrate mixture. The ratio, expressed as percent, of such change in optical density in each reaction mixture containing N (2,4 dinitrophenyl)-6-aminocaproate to that in the reaction mixture containing neither N (2,4 dinitrophenyl)-6-aminocaproate nor antibody to 2,4 dinitrophenyl was calculated and is referred to in Table 5 and FIG. 3 as the relative cycling rate. The results appear in Table 5 and in graphical form in FIG. 3 of the drawing.

TABLE 5

| reaction mixture | concentration of N (2,4 dinitrophenyl)-6-aminocaproate (nM) | relative cycling rate (%) |
| --- | --- | --- |
| 1 | 0 | 16 |
| 2 | 17 | 19 |
| 3 | 42 | 30 |
| 4 | 83 | 35 |
| 5 | 166 | 41 |
| 6 | 415 | 76 |

It was thus demonstrated in this Example that the relative cycling rate of the cycling reaction system, and thus the activity of the NAD in the NAD-dinitrophenyl conjugate, was a direct function of the amount of N (2,4 dinitrophenyl)-6-aminocaproate present in the specific binding reaction mixture. The present invention therefore provides a test composition and method for quantitatively determining the presence of the ligand N (2,4 dinitrophenyl)-6-aminocaproate in a liquid medium using a competitive binding-cycling assay technique.

EXAMPLE 10

Direct binding-bioluminesence assay for avidin; effect of presence of biotin on the peak light intensity produced.

The bioluminescence reaction system used in this Example was based on the following reactions:

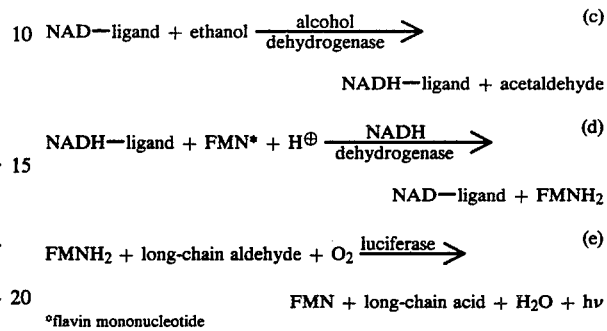

$$\text{NAD—ligand} + \text{ethanol} \xrightarrow{\text{alcohol dehydrogenase}} \quad \text{(c)}$$

$$\text{NADH—ligand} + \text{acetaldehyde}$$

$$\text{NADH—ligand} + \text{FMN}^* + \text{H}^\oplus \xrightarrow{\text{NADH dehydrogenase}} \quad \text{(d)}$$

$$\text{NAD—ligand} + \text{FMNH}_2$$

$$\text{FMNH}_2 + \text{long-chain aldehyde} + \text{O}_2 \xrightarrow{\text{luciferase}} \quad \text{(e)}$$

$$\text{FMN} + \text{long-chain acid} + \text{H}_2\text{O} + \text{h}\nu$$

*flavin mononucleotide

A light-generating solution for carrying out reactions (d) and (e) was prepared as follows. A reagent mixture was prepared containing 0.13M phosphate buffer at pH 7.0, 0.67 wt% bovine serum albumin, 15.7 μM flavin mononucleotide (FMN), and 13.3 mM sodium acetate, and this mixture was stored in the dark at −20° C. An emulsion of 5 μl of dodecanal in 5 ml of water was prepared the day the light-generating solution was to be used. Lyophilized luciferase extracted from Photobacterium fisheri (enzyme available from Worthington Biochemical Corp., Freehold, N.J.) was added to 0.013M phosphate buffer at pH 7.3 to a concentration of 20 mg/ml. After 30 minutes the resulting suspension was centrifuged at 1500×g for 10 minutes and the pellet was discarded. The light-generating solution was then prepared within 5 minutes of use by combining 75 μl of the reagent mixture, 5 μl of the dodecanal emulsion, and 20 μl of the luciferase solution.

To detect the light produced by reaction (e) a photometer was constructed consisting of a photodetector and a 6×50 mm cuvette mounted within a light integrating sphere such that light generated in the cuvette was reflected onto the photodetector. The electronic signal produced by the photodetector was passed to a strip chart recorder. The peak light intensity, as the term is used herein, was measured from the recorder trace and assigned arbitrary units based on the chart paper divisions.

Nine specific binding reaction mixtures were prepared, each having a total volume of 0.2 ml and each containing 0.1M tris-(hydroxymethyl)-aminomethane hydrochloride buffer at pH 8.0, 0.01M semicarbazide hydrochloride, and respectively the amounts or concentrations indicated in Table 6 of ethanol, NAD, NAD-biotin conjugate prepared as in Example 2, biotin, and avidin. The reaction mixtures were incubated at room temperature for 10 minutes. Then, 0.025 International units of alcohol dehydrogenase was added to each reaction mixture to initiate a reduction reaction. Semicarbazide combines with the acetaldehyde produced in reaction (c) to form a semicarbazone and thus to drive reaction (c) in the desired direction.

The reaction mixtures were incubated at room temperature for about 30 minutes. A 10 μl volume of each reaction mixture was then injected into a separate cuvette mounted in the photometer previously described and containing 100 μl of the previously prepared light-generating solution which had been pre-incubated at 28° C. for from 2 to 3 minutes. The results appear in Table 6.

TABLE 6

| reaction | concentration of ethanol (M) | concentration of NAD (nM) | concentration of NAD-biotin conjugate (nM) | concentration of biotin (nM) | avidin activity (units) | peak light intensity |
|---|---|---|---|---|---|---|
| 1 | — | 375 | — | — | — | 2 |
| 2 | 0.6 | 375 | — | — | — | 136 |
| 3 | 0.6 | 375 | — | — | 0.054 | 140 |
| 4 | — | — | 343 | — | — | 2 |
| 5 | 0.6 | — | 343 | — | — | 56 |
| 6 | 0.6 | — | 343 | — | 0.054 | 15 |
| 7 | — | — | 343 | 200 | 0.054 | 5 |
| 8 | 0.6 | — | 343 | 200 | 0.054 | 32 |
| 9 | 0.6 | — | 343 | 200 | — | 52 |

Reactions 1, 4, and 7 were controls and show that in the absence of ethanol essentially no reaction occurred. The result from reaction 5 demonstrates that the NAD-biotin conjugate is active in the bioluminescence reaction system. It can be seen from the results of reactions 5 and 6 that the presence of avidin in the reaction mixture inhibits the amount of light produced. From a comparison of the results of reactions 6 and 8 it is seen that the presence of free biotin reduces the amount of inhibition of light production as the concentration of biotin increases in the reaction mixture. Reactions 2 and 3 demonstrate that avidin does not inhibit the activity of free NAD and reactions 5 and 9 show that the presence of biotin alone does not affect the activity of the NAD-biotin conjugate.

It was thus demonstrated in this Example that the activity of the NAD in the NAD-biotin conjugate relative to the bioluminescense reaction system was decreased in the presence of avidin and that the magnitude of such decrease in activity was reduced by the additional presence of biotin.

EXAMPLE 11

Competitive binding-bioluminescence assay for biotin; effect of varying levels of biotin on the peak light intensity produced.

The bioluminescence reaction system used in this Example was the same as that diagrammed in Example 10. Seven specific binding reaction mixtures were prepared, each having a total volume of 0.2 ml and each containing 0.1M tris-(hydroxymethyl)-aminomethane hydrochloride buffer at pH 8.0, 0.6M ethanol, 0.01M semicarbazide hydrochloride, 343 nM NAD-biotin conjugate prepared as in Example 2, 0.025 International units of alcohol dehydrogenase, and 0.055 units of avidin. Biotin was added to six of the seven reaction mixtures, i.e. nos. 2 through 7 in Table 7, in the concentrations indicated in said Table. The order and manner of addition was the same as in Example 10.

Figure 4:
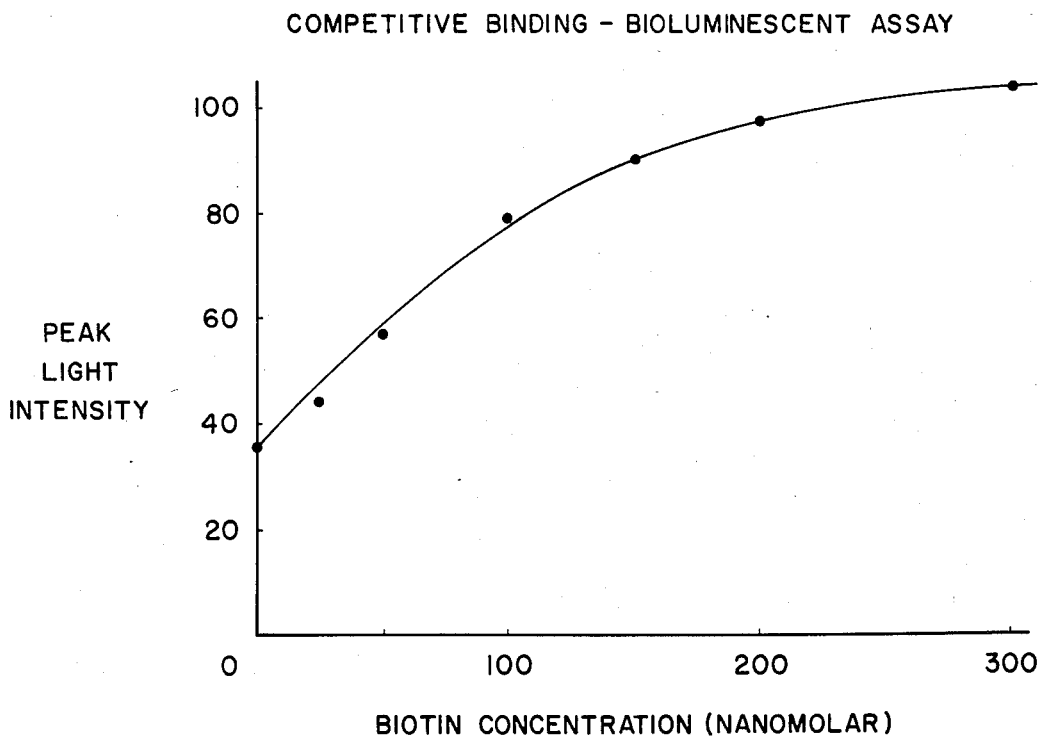
FIGS. 4 and 5, respectively, are graphical representations of the effect of various levels of two different ligands on the peak light intensity produced in a competitive binding-bioluminescence assay technique.

The reaction mixtures were incubated at room temperature for about 30 minutes. A 10 μl volume of each reaction mixture was injected into a separate cuvette mounted in the photometer described in Example 10 and containing 100 μl of a light-yielding solution prepared in the manner described in Example 10 and pre-incubated at 28° C. for from 2 to 3 minutes. The entire procedure was run in duplicate, and the averaged results appear in Table 7 and in graphical form in FIG. 4 of the drawing.

TABLE 7

| reaction mixture | concentration of biotin (nM) | average peak light intensity |
|---|---|---|
| 1 | 0 | 36 |
| 2 | 25 | 44 |
| 3 | 50 | 57 |
| 4 | 100 | 79 |
| 5 | 150 | 90 |
| 6 | 200 | 97 |
| 7 | 300 | 104 |

It was thus demonstrated in this Example that the magnitude of the peak light intensity produced by the bioluminescence reaction system, and thus the activity of the NAD in the NAD-biotin conjugate, was a direct function of the amount of biotin present in the specific binding reaction mixture. The present invention therefore provides a test composition and method for quantitatively determining the presence of the ligand biotin in a liquid medium using a competitive binding-bioluminescence assay technique.

EXAMPLE 12

Competitive binding-bioluminescence assay for 2,4 dinitrobenzene and derivatives thereof; effect of various levels of N (2,4 dinitrophenyl)-6-aminocaproate on the peak light intensity produced.

The bioluminescence reaction system used in this Example was the same as that diagrammed in Example 10. Seven specific binding reaction mixtures were prepared, each having a total volume of 0.1 ml and each containing 0.1M tris(hydroxymethyl)-aminomethane hydrochloride buffer at pH 8.0, 0.01M semicarbazide hydrochloride, 0.6M ethanol, 35 μM nicotinamide mononucleotide, and 367 nM NAD-dinitrophenyl conjugate prepared as in Example 3. N (2,4 dinitrophenyl)-6-aminocaproate was added to six of the seven reaction mixtures, i.e. nos. 2 through 7 in Table 8, at the concentrations indicated in said Table, and to each of said six reaction mixtures was also added an amount of antibody to 2,4 dinitrophenyl sufficient to reduce the peak light intensity produced to 39% of that produced in the absence of N (2,4 dinitrophenyl)-6-aminocaproate and antibody to 2,4 dinitrophenyl.

Figure 5:
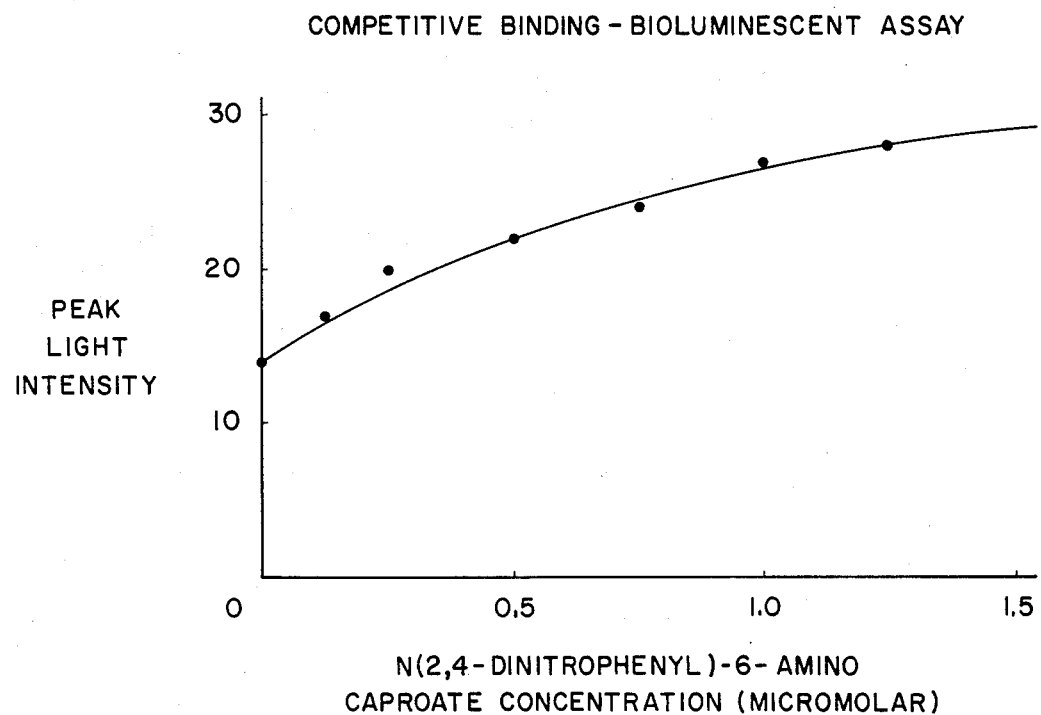

The reaction mixtures were incubated at room temperature for 3 hours. Then, 0.025 International units of alcohol dehydrogenase was added to each reaction mixture to initiate a reduction reaction. The reaction mixtures were then incubated at room temperature for about 30 minutes. A 10 μl volume of each reaction mixture was injected into a separate cuvette mounted in the photometer described in Example 10 and containing 100 μl of a light-generating solution prepared in the manner described in Example 10 and pre-incubated at 28° C. for from 2 to 3 minutes. The entire procedure was run in duplicate, and the averaged results appear in Table 8 and in graphical form in FIG. 5 of the drawing.

TABLE 8

| reaction mixture | concentration of N (2,4 dinitrophenyl)-6-aminocaproate (μM) | average peak light intensity |
|---|---|---|
| 1 | 0.00 | 14 |
| 2 | 0.125 | 17 |
| 3 | 0.25 | 20 |
| 4 | 0.50 | 22 |
| 5 | 0.75 | 24 |
| 6 | 1.00 | 27 |
| 7 | 1.50 | 28 |

It was thus demonstrated in this Example that the magnitude of the peak light intensity produced by the bioluminescence reaction system, and thus the activity of the NAD in the NAD-2,4 dinitrophenyl conjugate, was a direct function of the amount of N (2,4 dinitrophenyl)-6-aminocaproate present in the specific binding reaction. The present invention therefore provides a test composition and method for quantitatively determining the presence of the ligand N (2,4 dinitrophenyl)-6-aminocaproate in a liquid medium using a competitive binding-bioluminescence assay technique.

EXAMPLE 13

Specific binding assays for biotin and avidin employing an enzyme substrate as labeling substance.

The specific binding assay system used in this Example was based on the following reaction:

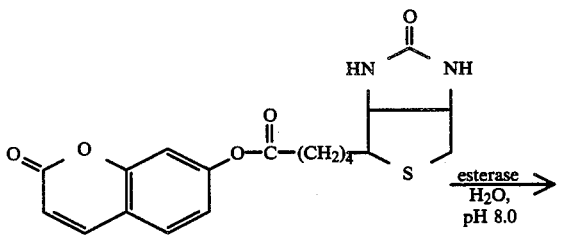

umbelliferone-biotin conjugate
(maximum fluorescence at 378 nm)

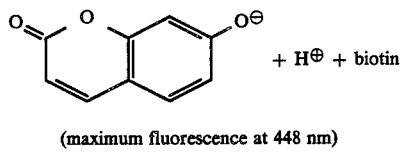

(maximum fluorescence at 448 nm)

Ten specific binding reaction mixtures were prepared, each having a total volume of 0.3 ml and each containing 0.1M tris-(hydroxymethyl)-aminomethane hydrochloride buffer at pH 8.0 and the respective amounts or concentrations of umbelliferone-biotin conjugate prepared as in Example 4, biotin, and avidin indicated in Table 9. The reaction mixtures were incubated at room temperature for from 1 to 3 minutes. Reaction mixtures nos. 2 through 10 in Table 9 each also contained 0.26 International units of bovine liver carboxylate hydrolase (esterase). The relative reaction rate in each of the reaction mixtures was then determined by monitoring the fluorescence produced by each thereof at 448 nm with a Model 111 Turner fluorometer (available from G. K. Turner Assoc., 2524 Pulgas Street, Palo Alto, Calif.) set for excitation at 364 nm. The electronic signal produced by the fluorometer was passed to a strip chart recorder, and the amount of fluorescence produced per minute was measured from the recorder trace and assigned arbitrary units based on the chart paper divisions. The results appear in Table 9.

TABLE 9

| reaction | esterase (I.U.) | concentration of umbelliferone-biotin conjugate (nM) | concentration of biotin (nM) | avidin activity (units) | change in fluorescence/min. |
|---|---|---|---|---|---|
| 1 | — | 730 | — | — | 0.000 |
| 2 | 0.26 | 365 | — | — | 0.077 |
| 3 | 0.26 | 730 | — | — | 0.145 |
| 4 | 0.26 | 730 | — | 0.0022 | 0.103 |
| 5 | 0.26 | 730 | — | 0.022 | 0.058 |
| 6 | 0.26 | 730 | — | 0.055 | 0.000 |
| 7 | 0.26 | 730 | — | 0.033 | 0.027 |
| 8 | 0.26 | 730 | — | 0.033 | 0.026 |
| 9 | 0.26 | 730 | 670 | 0.033 | 0.057 |
| 10 | 0.26 | 730 | 1340 | 0.033 | 0.115 |

Reaction 1 was a control and shows that in the absence of esterase no reaction occurs. The results of reactions 2 and 3 demonstrate that the umbelliferone-biotin conjugate was active in the enzymatic reaction, and comparing such results to those of reactions 4 through 8 demonstrates that the presence of avidin inhibits the reaction rate in proportion to the amount of avidin in the reaction mixture. Comparing the results of reactions 8, 9, and 10 shows that the amount of inhibition of the reaction rate by avidin is a direct function of the amount of biotin present in the reaction mixture.

It was thus demonstrated in this Example that the rate of fluorescence produced by the esterase reaction, and thus the substrate activity of the umbelliferone-biotin conjugate, was decreased by the presence of avidin and that the magnitude of such decrease in activity was reduced by the presence of biotin. The present invention therefore provides a test composition and method for determining the presence of the ligands biotin and avidin in a liquid medium using a specific binding assay technique employing an enzyme substrate as the labeling substance.

EXAMPLE 14

Preparation of 2,4-dinitrophenyl-fluorescein conjugate.

Fluorescein-3'-[6-(2,4-dinitroanilino)hexanoate].

The synthesis basically involved the reaction of the acid chloride of 6-(2,4-dinitroanilino)hexanoic acid with the disodium salt of fluorescein. 6-(2,4-dinitroanilino)-hexanoic acid was prepared by the method described in *Biochem. J.* 42: 287-94 (1948).

A solution of 1.5 g (5 mmol) of 6-(2,4-dinitroanilino)-hexanoic acid was converted to the acid chloride by reaction with 10 ml of warm thionyl chloride for 15 min followed by cooling and dilution with 20 ml of hexane. The solid acid chloride which formed was collected by filtration and after thorough drying was added to 600 mg of the disodium salt of fluorescein in 10 ml of dry acetone. After 5 hr at reflux, the reaction was quenched by the addition of 2 ml water and 5 ml acetone. After 30 min at 25° C., the mixture was concentrated to dryness and the residue partitioned between ethyl acetate and aqueous sodium bicarbonate solution. The organic phase was separated and washed with 1% aqueous sulfuric acid, dried over anhydrous magnesium sulfate and evaporated. The red oil was chromatographed on 60 g of silica gel 60, available from E. Merck, Darmstadt, Germany, with 20% (v/v) acetone in carbon tetrachloride as eluant. The 1.2 g of impure bis-ester was rechromatographed on 60 g of silica gel using 10% (v/v) acetone in carbon tetrachloride. Appropriate fractions were combined and evaporated to yield 180 mg of a yellow, glassy solid.

Calculated for $C_{44}H_{38}N_6O_{15}$: C, 59.33; H, 4.30; N, 9.43 Found: C, 60.92; H, 4.35; N, 6.65.

The infrared spectrum displayed the expected ester carbonyl stretching absorption at 1765 cm$^{-1}$.

EXAMPLE 15

Specific binding assays for derivatives of 2,4-dinitrophenyl and antibody thereto employing an enzyme substrate (modified fluorescein) as labeling substance.

The specific binding assay systems used in this Example was based on the reaction shown in Diagram 1.

A. Direct binding-fluorescent assay for antibody to 2,4-dinitrophenyl; effect of various levels of antibody on the reaction rate.

Seven specific binding reaction mixtures were prepared and analyzed. For each reaction mixture, 20 μl of 1 μM 2,4-dinitrophenyl-fluorescein conjugate (prepared according to Example 14) in dimethylsulfoxide was combined with a volume of antiserum to 2,4-dinitrophenyl as indicated in Table 10 and with a sufficient volume of 0.1M bis-hydroxyethylglycine hydrochloride buffer at pH 7.0 to make a total volume of 2.0 ml. The background rate of hydrolysis of the ester linkage in the conjugate was determined for three minutes for each reaction mixture by determining the rate of increase of fluorescence intensity at 510 nm using the general technique described in Example 13 with the fluorometer set for excitation at 470 nm.

DIAGRAM 1

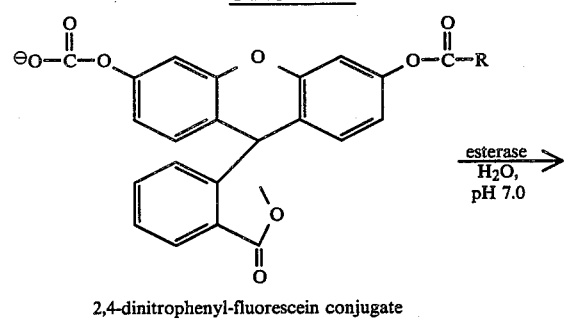

2,4-dinitrophenyl-fluorescein conjugate

-continued
DIAGRAM 1

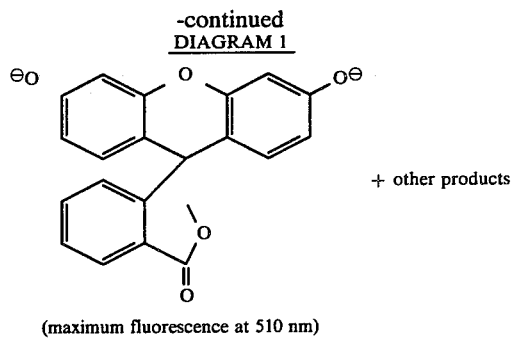

+ other products (maximum fluorescence at 510 nm)

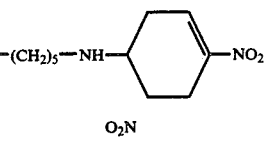

Figure 6:
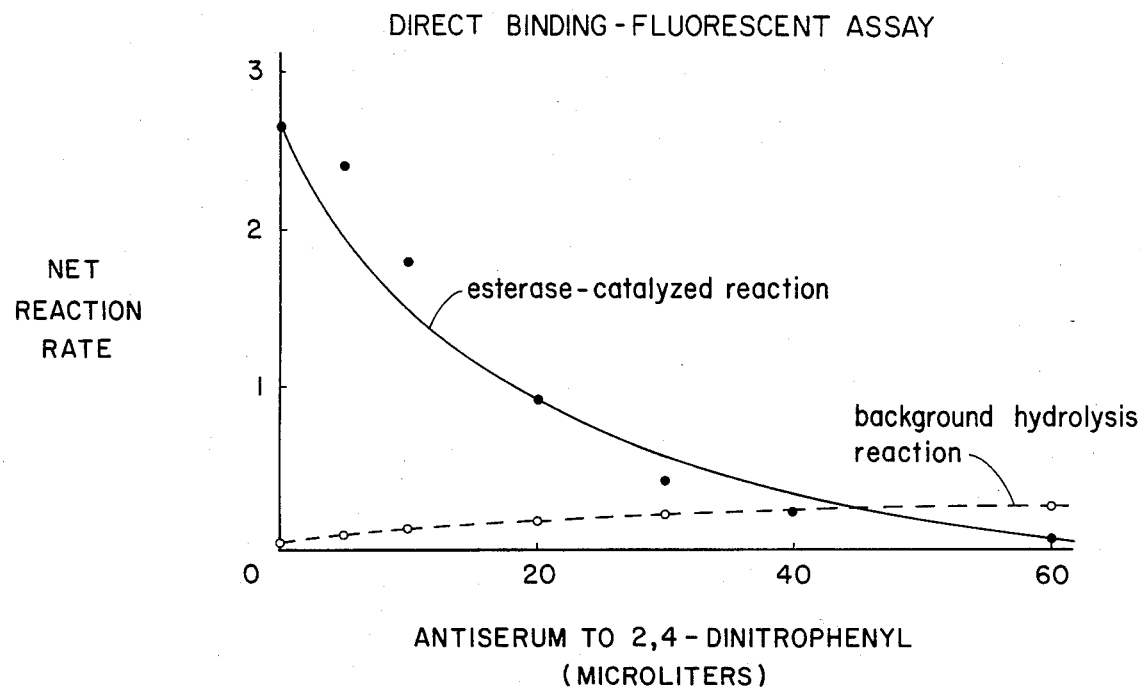
FIG. 6 is a graphical representation of the effect of various levels of a ligand on the net rates of two different reactions, one enzyme-catalyzed and the other not, in a direct binding-fluorescent assay technique.

A 10 μl volume of 0.1M bis-hydroxyethylglycine hydrochloride buffer at pH 7.0 containing 0.54 units of Type I esterase (E.C. No. 3.1.1.1, obtained from Sigma Chemical Co., St. Louis, Mo.) was then added to each reaction mixture. The resulting overall reaction rate was measured in the same manner as the background hydrolysis rate. The results appear in Table 10. The background hydrolysis rate was substrated from the overall reaction rate to obtain the net reaction rate attributable to the esterase-catalyzed reaction. The relationships between both the net enzyme-catalyzed reaction rate and the background alkaline hydrolysis reaction rate and the amount of antiserum present in the reaction mixture is shown in graphical form in FIG. 6 of the drawing.

TABLE 10

| reaction mixture | amount of antiserum (μl) | background hydrolysis rate | overall reaction rate |
|---|---|---|---|
| 1 | 0 | 0.02 | 2.68 |
| 2 | 5 | 0.07 | 2.48 |
| 3 | 10 | 0.11 | 1.91 |
| 4 | 20 | 0.17 | 1.08 |
| 5 | 30 | 0.21 | 0.63 |
| 6 | 40 | 0.22 | 0.45 |
| 7 | 60 | 0.26 | 0.30 |

It was demonstrated in this part of the Example that the net reaction rate of the hydrolysis reaction was an inverse function of the amount of antibody to the ligand, 2,4-dinitrophenyl, present in the specific binding reaction mixture. It was likewise demonstrated that the reaction rate of the background hydrolysis reaction was a direct function of the amount of antibody present in the specific binding reaction mixture. The present invention therefore provides a test composition and method for determining the presence of the ligand antibody to 2,4-dinitrophenyl in a liquid medium using a direct binding-fluorescent assay technique.

B. Competitive binding-fluorescent assay for derivatives of 2,4-dinitrophenyl; effect of various levels of 2,4-dinitrophenyl-β-alanine on the reaction rate.

Figure 7:
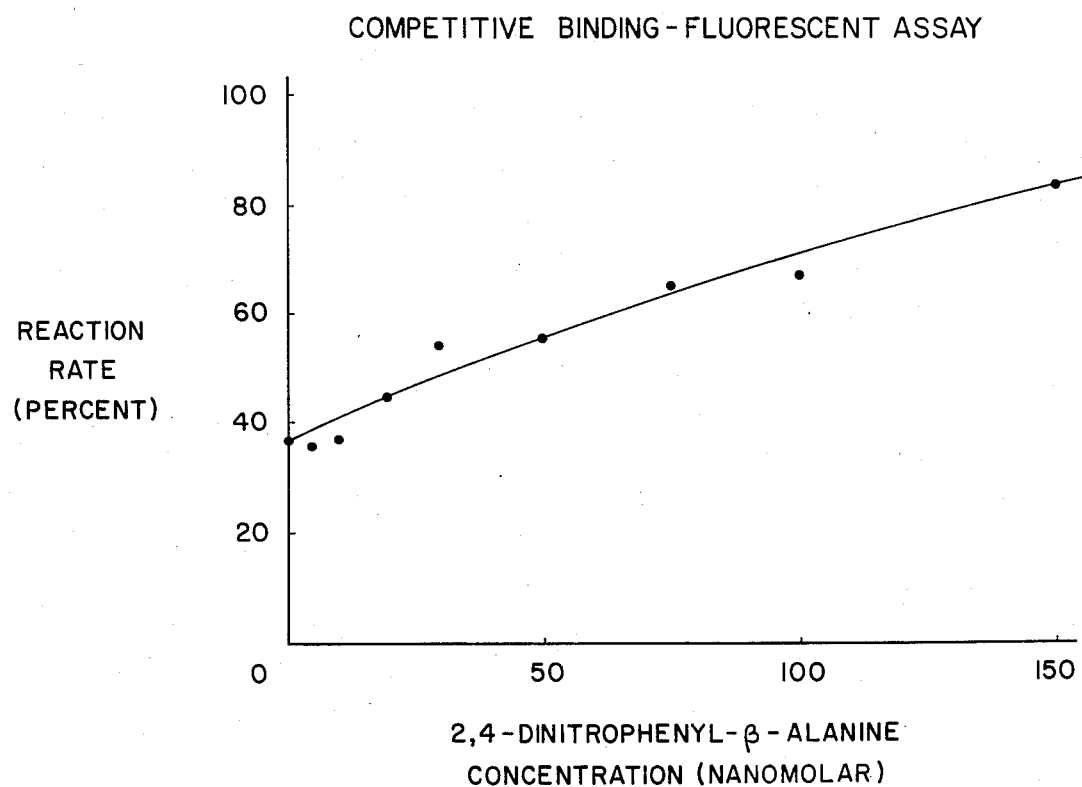
FIGS. 7 and 8, respectively, are graphical representations of the effect of various levels of a ligand on reaction rates in two different competitive binding assay techniques, one involving a fluorescent monitoring reaction and the other involving a spectrophotometric monitoring reaction.

Ten specific binding reaction mixtures were prepared, each having a total volume of 2.0 ml and each containing 0.1M bis-hydroxyethylglycine hydrochloride buffer at pH 7.0 and 2,4-dinitrophenyl-β-alanine, prepared according to the method described in J. Amer. Chem. Soc. 76: 1328 (1954), at the concentrations indicated in Table 11. To nine of the ten reaction mixtures, i.e. nos. 2 through 10 in Table 11, was added an amount of antiserum to 2,4-dinitrophenyl sufficient to inhibit the rate of the esterase-catalyzed reaction in the other mixture, i.e. no. 1, by 60 percent. After mixing, 20 μl of 1 μM 2,4-dinitrophenyl-fluorescein conjugate (prepared as in Example 14) in dimethylsulfoxide was added to each reaction mixture. A 10 μl volume of 0.1M bis-hydroxyethylglycine hydrochloride buffer at pH 7.0 containing 0.54 units of Type I esterase (E.C. No. 3.1.1.1, obtained from Sigma Chemical Co., St. Louis, Mo.) was then added to each reaction mixture. The resulting reaction rate was measured as in Part A of this Example. The percentage value of the rate of reactions nos. 2 through 10 to that of reaction no. 1 (no antibody present) was calculated. The results appear in Table 11 and in graphical form in FIG. 7 of the drawing.

TABLE 11

| reaction mixture | concentration of 2,4-dinitrophenyl-β-alanine (nM) | reaction rate | percent of rate of reaction no. 1 |
| --- | --- | --- | --- |
| 1 | 0 | 2.78 | — |
| 2 | 0 | 1.04 | 37 |
| 3 | 5 | 1.01 | 36 |
| 4 | 10 | 1.04 | 37 |
| 5 | 20 | 1.24 | 45 |
| 6 | 30 | 1.51 | 54 |
| 7 | 50 | 1.54 | 56 |
| 8 | 75 | 1.80 | 65 |
| 9 | 100 | 1.85 | 67 |
| 10 | 150 | 2.33 | 84 |

It was demonstrated in this part of the Example that the reaction rate of the hydrolysis reaction was a direct function of the amount of 2,4-dinitrophenyl-β-alanine in the reaction mixture. The present invention therefore provides a test composition and method for determining the presence of ligands such as derivatives of 2,4-dinitrophenyl in a liquid medium using a competitive binding-fluorescent assay technique.

C. Competitive binding-spectrophotometric assay for derivatives of 2,4-dinitrophenyl; effect of various levels of 2,4-dinitrophenyl-β-alanine on the reaction rate.

Figure 8:
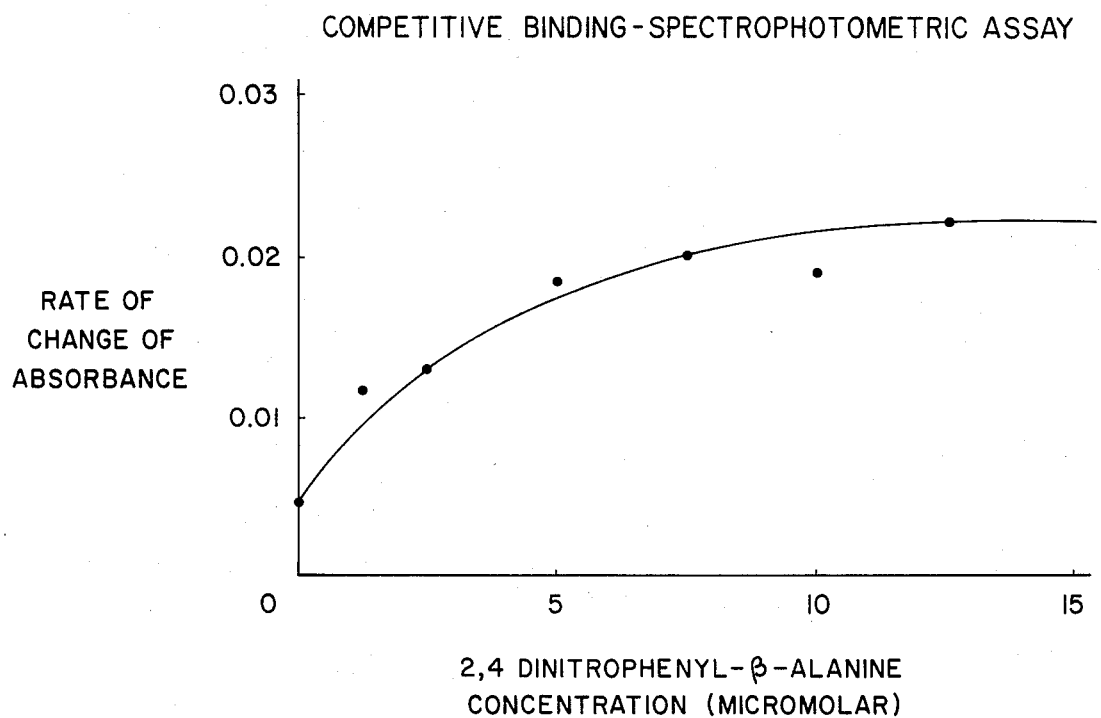

Eight specific binding reaction mixtures were prepared, each having a total volume of 1.0 ml and each containing 0.1M tris-(hydroxymethyl)-aminomethane hydrochloride buffer at pH 7.0 and 2,4-dinitrophenyl-β-alanine at the concentrations indicated in Table 12. To seven of the eight reaction mixtures, i.e. nos 2 through 8 in Table 12, was added an amount of antiserum to 2,4-dinitrophenyl sufficient to inhibit the rate of the esterase-catalyzed reaction in the other mixture, i.e. no. 1, by 82 percent. After mixing, 10 μl of 0.1 mM 2,4-dinitrophenyl-fluorescein conjugate (prepared as in Example 14) in dimethylsulfoxide was added to each reaction mixture. A 20 μl volume of 0.1M tris-(hydroxymethyl)-aminomethane hydrochloride buffer at pH 7.0 containing 2.16 International units of Type I esterase (E.C. No. 3.1.1.1, obtained from Sigma Chemical Co., St. Louis, Mo.) was then added to each reaction mixture. The change in absorbance of each reaction mixture at 489 nm per minute was recorded with a Gilford 2000 spectrophotometer. The results appear in Table 12 and in graphical form in FIG. 8 of the drawing.

TABLE 12

| reaction mixture | concentration of 2,4-dinitrophenyl-β-alanine (μM) | rate of change of absorbance |
| --- | --- | --- |
| 1 | 0 | 0.0261 |

TABLE 12-continued

| reaction mixture | concentration of 2,4-dinitrophenyl-β-alanine (μM) | rate of change of absorbance |
| --- | --- | --- |
| 2 | 0 | 0.0047 |
| 3 | 1.25 | 0.0118 |
| 4 | 2.5 | 0.0131 |
| 5 | 5.0 | 0.0185 |
| 6 | 7.5 | 0.0202 |
| 7 | 10.0 | 0.0192 |
| 8 | 12.5 | 0.0223 |

It was demonstrated in this part of the Example that the reaction rate was a direct function of the amount of 2,4-dinitrophenyl-β-alanine in the reaction mixture. The present invention therefore provides a test composition and method for determining the presence of ligands such as derivatives of 2,4-dinitrophenyl in a liquid medium using a competitive binding-spectrophotometric assay technique.

D. Competitive binding-fluorescent assay for derivatives of 2,4-dinitrophenyl; use of non-enzymatic monitoring reaction.

The specific binding assay system used in this part was the same as shown in Diagram 1 except that no esterase was used to catalyze the hydrolysis of the ester linkage in the conjugate.

Eight specific binding reaction mixtures were prepared, each having a total volume of 2 ml and each containing 0.1M tris-(hydroxymethyl)-aminomethane hydrochloride buffer at pH 7.5 and 2,4-dinitrophenyl-β-alanine at the concentrations indicated in Table 13. To each reaction mixture was added 50 μl of antiserum to 2,4-dinitrophenyl. After mixing, 20 μl of 2 μM 2,4-dinitrophenyl-fluorescein conjugate (prepared as in Example 14) in dimethylsulfoxide was added to each reaction mixture and the resulting reaction rate was measured as in Part A of this Example. The results appear in Table 13.

TABLE 13

| reaction mixture | concentration of 2,4-dinitrophenyl-β-alanine (nM) | reaction rate |
| --- | --- | --- |
| 1 | 0 | 0.96 |
| 2 | 12.5 | 0.94 |
| 3 | 31.2 | 0.84 |
| 4 | 62.5 | 0.78 |
| 5 | 94.0 | 0.70 |
| 6 | 125 | 0.59 |
| 7 | 187 | 0.57 |
| 8 | 250 | 0.53 |

It was demonstrated in this part of the Example that the background hydrolysis rate, in the absence of esterase, was an inverse function of the amount of 2,4-dinitrophenyl-β-alanine in the reaction mixture. The present invention therefore provides a test composition and method for determining the presence of ligands such as derivatives of 2,4-dinitrophenyl in a liquid medium using a competitive binding-fluorescent technique wherein the binding partner, upon becoming bound to the ligand in the conjugate, participates in the monitoring reaction.

EXAMPLE 16

Preparation of cortisol-umbelliferone conjugate.
Cortisol-21-hemisuccinate-umbelliferone.
A. Cortisol-21-hemisuccinate.

Succinic anhydride (0.5 g) was added to a solution of 0.5 g cortisol in 10 ml dry pyridine and stirred overnight at room temperature. Water (100 ml) was added and the mixture extracted with 100 ml ethyl acetate. The organic phase was washed once with water and extracted with 100 ml saturated sodium bicarbonate solution. The aqueous phase was separated and acidified to pH 4 with 10% hydrochloric acid. The precipitate which formed was collected by filtration, dried, and recrystallized from a hexane-acetone mixture to yield the desired intermediate (meeting point=171°-2° C.).

B. Cortisol-umbelliferone conjugate.

Carbodiimide (50 mg) was added to a solution of 100 mg of the intermediate from Part A of this Example in 3 ml dry dimethylformamide and stirred for 30 minutes. A solution of 50 mg 7-hydroxycoumarin in 2 ml dimethylformamide was added and the reaction mixture was stirred overnight at room temperature. The precipitate which formed was filtered and discarded. Water was added to the filtrate and the mixture was extracted with ethyl acetate. The organic phase was washed once with water, separated, dried with anhydrous sodium sulfate, filtered, and evaporated to dryness under vacuum. The residue was crystallized from an acetone-hexane mixture yielding the desired conjugate (melting point=126° C.).

EXAMPLE 17

Specific binding assay for cortisol employing an enzyme substrate (modified umbelliferone) as labeling substance.

The specific binding assay system used in this Example was based on the following reaction:

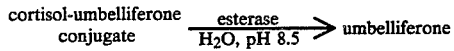

Eight specific binding reaction mixtures were prepared, each having a total volume of 2 ml and each containing 0.1M bis-hydroxyethylglycine hydrochloride buffer at pH 8.5 and cortisol at the concentrations indicated in Table 14. To seven of the eight reaction mixtures, i.e. nos. 2 through 8 in Table 14, was added an amount of antiserum to cortisol sufficient to inhibit the rate of the esterase-catalyzed reaction in the other reaction mixture, i.e. no. 1, by 70 percent. After mixing, 20 μl of 2 μM cortisol-umbelliferone conjugate (prepared as in Example 16) in 0.1M bis-hydroxyethylglycine hydrochloride buffer at pH 8.5 was added to each reaction mixture. After mixing again, 15 μl of porcine esterase (0.81 units/ml) were added to each reaction mixture. The resulting reaction rate was measured in each reaction mixture in a manner similar to that described in Example 13. The results appear in Table 14.

TABLE 14

| reaction mixture | concentration of cortisol (nM) | reaction rate |
|---|---|---|
| 1 | 0 | 0.0838 |
| 2 | 0 | 0.0256 |
| 3 | 2.5 | 0.0296 |
| 4 | 10 | 0.0306 |
| 5 | 20 | 0.0381 |
| 6 | 30 | 0.0408 |
| 7 | 50 | 0.0654 |
| 8 | 100 | 0.0603 |

It was demonstrated in this Example that the reaction rate was a direct function of the amount of cortisol in the reaction mixture. The present invention therefore provides a test composition and method for determining the presence of cortisol in a liquid medium using a competitive binding-fluorescent assay technique.

EXAMPLE 18

Preparation of 2,4-dinitrophenyl-ATP conjugate (6-position derivative).

$N^6$-[2-(2,4-dinitrophenyl)aminoethyl]adenosine-5'-triphosphate.

A. $N^6$-(2-aminoethyl)adenosine-5'-monophosphate.

Two g (7 mmol) 6-chloropurine riboside (available from Sigma Chemical Co., St. Louis, Mo.) was stirred with 17 ml triethylphosphate and was reacted with phosphoryl chloride in the presence of water as described in Chem. Scrip. 19: 165–70 (1972). After hydrolysis of the phosphodichloridate, 9.5 ml ethylenediamine (140 mmol) was added and allowed to react at room temperature for 3 hr. The reaction mixture was diluted to 4 liters with water and adjusted to pH 12 with sodium hydroxide. This solution was passed through a 5×30 cm column of Dowex 1×8 (available from Bio-Rad Laboratories, Richmond, Calif.) in the acetate form. Then the column was washed with 3 liters 0.01M ammonium chloride and the chromatogram was developed with a linear gradient generated with 3 liters water and 3 liters 1M acetic acid. An isolated peak of uv absorbing material eluted between 1800 ml and 2050 ml of the gradient was concentrated to about 25 ml under vacuum. While this solution stood at 7° C. overnight, white crystals formed and these were collected and dried to give 65 percent yield of the product. A sample was recrystallized from hot water for analysis. Calculated for $C_{12}H_{19}N_6O_7P\cdot2H_2O$: C, 33.8; H, 5.45; N, 19.7. Found: C, 34.3; H, 5.22; N, 19.7. Separate thin-layer chromatograms developed with two solvent systems, the first consisting of 4 parts 0.5M ammonium acetate to 1 part ethanol and the second consisting of 3 parts isobutyric acid to 5 parts 1M ammonium hydroxide, each showed one component which quenched fluorescence and reacted with ninhydrin. The compound in 0.1N hydrochloric acid had an absorption maximum at 264 nm and the millimolar extinction coefficient was 17.7 which spectral properties are characteristic of $N^6$-alkylated adenosine derivatives.

B. $N^6$-[2-(2,4-dinitrophenyl)aminoethyl]adenosine-5'-monophosphate.

Two hundred fifty mg $N^6$-(2-aminoethyl)adenosine-5'-monophosphate (0.65 mmol) from Part A of this Example was dissolved in 20 ml water at pH 8. Then 168 mg sodium bicarbonate was added, followed by 0.2 ml 1-fluoro-2,4-dinitrobenzene (1.58 mmol dissolved in 2 ml ethanol). The reaction mixture was stirred in the dark at room temperature for 4 hr and then an additional 0.1 ml 1-fluoro-2,4-dinitrobenzene in 1 ml ethanol was added. After the reaction mixture had stirred overnight, it was adjusted to pH 2.0 with hydrochloric acid and was poured into 200 ml ethanol. The precipitate which formed was dissolved in 200 ml water and this solution was adjusted to pH 8.0 with sodium hydroxide and chromatographed on a 2.5×30 cm column of DEAE-cellulose in the bicarbonate form (available from Reeve Angel, Clifton, N.J.). The chromatogram was developed with a linear gradient generated with 1.5 liters water and 1.5 liters 0.7M ammonium bicarbonate. A major peak of yellow material which absorbed uv light was eluted between 1200 and 1500 ml of the gradient. Ammonium bicarbonate was removed by repeated evaporation to dryness to give 40 percent yield of the desired product. This product migrated as one yellow spot on thin-layer chromatograms developed with the same two solvents mentioned in Part A of this Example and on epichlorohydrintriethanolamine anion-exchange paper developed with 0.25M sodium acetate-acetic acid buffer, pH 5.0. In 0.02N hydrochloric acid the product had optical absorption maxima of 264 nm and 363 nm with millimolar extinction coefficients of 21.8 and 14.2, respectively.

C. 2,4-dinitrophenyl-ATP conjugate.

$N^6$-[2-(2,4-dinitrophenyl)aminoethyl]adenosine-5'-monophosphate (from Part B of this Example) (0.3 mmole) was converted to the pyridinium salt by chromatography on a 1.5×20 cm column of Dowex 50×2 in the pyridinium form (available from Bio-Rad Laboratories, Richmond, Calif.). The yellow effluent was concentrated to dryness and 15 ml dimethylformamide and 0.3 mmol tri-n-butylamine were added. This mixture was evaporated to dryness and the residue was dried further by repeated evaporation. The monophosphate intermediate was then converted to the triphosphate form using the method disclosed in *J. Amer. Chem. Soc.* 87: 1785-8 (1965). The reaction products which were soluble in dimethylformamide were added to 250 ml water which was then adjusted to pH 8.0. This solution was passed into a 2.5×58 cm column of DEAE-cellulose in the bicarbonate form and the chromatogram was developed with a linear gradient generated with 3 liters water and 3 liters 0.5M ammonium carbonate. The first eluted peak of yellow material was identified as the diphosphate derivative. A second peak of yellow material, which eluted between 4.15 and 4.4 liters of the gradient, was evaporated to dryness to give 20 percent yield of the desired conjugate which, by analysis, was found to contain 3.0 residues of phosphate per ribose residue.

EXAMPLE 19

Preparation of 2,4-dinitrophenyl-ATP conjugate (8-position derivative).

8-[2-(2,4-dinitrophenyl)aminoethyl]aminoadenosine-5'-triphosphate.

A. 8-(2-aminoethyl)aminoadenosine-5'-monophosphate.

A reaction mixture consisting of 2.2 mmol 8-bromoadenosine-5'-monophosphate, prepared according to the method described in *Arch. Biochem. Biophys.* 163: 561-9 (1974), 66 mmol ethylenediamine and 25 ml water was heated in an oil bath at 140° for 2 hr. The cooled mixture was adjusted to pH 11.5 with sodium hydroxide and passed into a 2.5×55 cm column of Dowex 1×8 (200-400 mesh, bicarbonate form). The column was washed with 300 ml water and then with a linear gradient generated with 3 liters water and 3 liters 0.5M ammonium bicarbonate. The absorbance of the effluent at 254 nm was monitored and a major peak of absorbing material eluted between 4.6 and 5.8 liters of the gradient.

Ammonium bicarbonate was removed by repeated evaporation (five times, 20 to 30 ml water each time) to dryness under vacuum and the final residue was dissolved in 20 ml water by addition of ammonium hydroxide to pH 8.0. The solution was filtered, adjusted to pH 5.0 with formic acid and allowed to stand at 5° C. for one day. Crystals which formed were collected, dissolved at pH 8.0 and recrystallized at pH 5.0. The yield of the desired intermediate was 27 percent. On examination by thin layer chromatography in a solvent consisting of 4 parts 0.5M ammonium acetate to 1 part ethanol, the product migrated as one ninhydrin positive spot which quenched fluorescence. The optical absorption maxiumum in 0.02N hydrochloric acid was 275 nm and the millimolar extinction coefficient was 17.5, which spectral properties are characteristic of alkylated 8-aminoadenosine derivatives. Calculated for $C_{12}H_{20}N_7O_7P \cdot H_2O$: C, 34.0; H, 5.33; N, 23.2. Found: C, 34.1; H, 5.28; N, 23.9.

B. 8-[2-(2,4-dinitrophenyl)aminoethyl]aminoadenosine-5'-monophosphate.

8-(2-aminoethyl)aminoadenosine-5'-monophosphate from Part A of this Example (0.64 mmol) was dissolved in 20 ml water by addition of sodium hydroxide to pH 8.0. Then 168 mg sodium bicarbonate was added, followed by 0.2 ml 1-fluoro-4-dinitrobenzene (1.58 mmol dissolved in 2 ml ethanol). The reaction was stirred for 18 hr at room temperature and then 0.1 ml 1-fluoro-2,4-dinitrobenzene in 1 ml ethanol was added. After stirring for an additional 4 hrs, the mixture was adjusted to pH 2.0 with hydrochloric acid and poured into 200 ml cold acetone (−10° C.). The yellow precipitate which formed was collected by filtration, dissolved in 200 ml water and passed into a 2.5×45 cm column of DEAE-cellulose in the bicarbonate form. The chromatogram was developed with a linear salt gradient generated with 2 liters water and 2 liters 0.7M ammonium carbonate. A peak of yellow material with an absorption maximum at 275 nm eluted between 2 and 3 liters of the gradient. Ammonium bicarbonate was removed from this material by evaporation under vacuum and the yield of the desired intermediate was 37 percent. Optical absorption maxima measured in 0.02N hydrochloric acid occurred at 275 and 363 nm and the millimolar extinction coefficients were 21.8 and 15.5, respectively. Further analyses showed 1.07 phosphate residue per ribose residue.

C. 2,4-dinitrophenyl-ATP conjugate.

The monophosphate intermediate (0.5 mmol) was converted to the tri-n-butylammonium salt by addition of 0.8 mmol tri-n-butylamine. The mixture was dried by repeated evaporation from dry dimethylformamide (four times, 10-15 ml each). The final residue, dissolved in 1 ml dimethylformamide, was mixed with 2.0 mmol carbonyldiimidazole also in 1 ml dimethylformamide and was allowed to react at room temperature for 4 hr. The excess carbonyldiimidazole was destroyed by reaction with 15 μl methanol for 30 min. Finally, 3 mmol tri-n-butylammonium pyrophosphate in 4 ml dimethylformamide was added and allowed to react for 20 hr. The solid residue which formed was separated by centrifugation and washed twice with 5 ml portions of dimethylformamide. The combined supernatants were added to 200 ml water, which was then adjusted to pH 8 and chromatographed on a 2.5×25 cm column of DEAE-cellulose in the bicarbonate form. The chromatogram was developed with a linear gradient generated with 2 liters water and 2 liters 0.5M ammonium bicarbonate. A peak of yellow material with an optical absorption maxima at 275 and 363 nm was eluted between 2.0 and 2.9 liters of the gradient. The ammonium bicarbonate was removed by evaporation to give a 22 percent yield of the desired conjugate. Results of analyses indicated that this product contained 3.2 residues of phosphate per residue of ribose.

EXAMPLE 20

Preparation of 2,4-dinitrophenyl-ATP conjugate (terminal phosphate derivative).

$P^1\{2-[N-(2,4-dinitrophenyl)amino]ethyl\}P^4-(5'-adenosine)$tetraphosphate.

A. 2-[N-(2,4-dinitrophenyl)amino]ethylphosphate.

A solution containing 20 mmol ethanolamine phosphate, 0.4 mol sodium bicarbonate and 0.2 g benzyltriethylammonium chloride in 20 ml water was stirred while 20 mmol 1-fluoro-2,4-dinitrobenzene was added dropwise. The resulting two-phase mixture was stirred at room temperature for 3 days. Then 600 ml ethanol was added and a yellow solid formed at 0° C. overnight. The solid was dissolved in 50 ml water and the solution was adjusted to pH 1.5 with 3N hydrochloric acid. The precipitate which formed was collected by filtration and triturated at 0° with 200 ml anhydrous ethanol. The solid residue was dried in a vacuum at room temperature to yield 4 gm of yellow product (65 percent of theoretical). This material melted at 200°–202° and migrated as one yellow spot on thin-layer chromatograms developed with a solvent consisting of 7 parts ethanol to 3 parts triethylammonium bicarbonate (pH 7.5). The optical absorption spectrum measured in 0.02N hydrochloric acid had maxima at 359 and 264 nm and the millimolar extinction coefficients were 17.0 and 9.2, respectively. The neutralization equivalent was 325 which is the value calculated for the monohydrate. Calculated for $C_8H_{10}N_3O_8P \cdot H_2O$: C, 29.55; H, 3.72; N, 12.92. Found: C, 29.38; H, 2.94; N, 12.81.

B. 2,4-dinitrophenyl-ATP conjugate.

The intermediate prepared in Part A of this Example was reacted with diphenylphosphorochloridate by the method described in *Eur. J. Biochem.* 23: 492–6 (1972) to produce the activated pyrophosphate which was reacted with ATP. One g 2-[N-(2,4-dinitrophenol)amino]ethylphosphate (3.25 mmol) was converted to the pyridinium salt by chromatography on a 2.5×25 cm column of Dowex 50×2 in the pyridinium form. The yellow effluent was concentrated to dryness and the residue was suspended in 50 ml methanol to which 1.4 ml tri-n-octylamine (3.25 mmol) was added. The mixture was stirred until the solid dissolved and then the methanol was removed under vacuum. The residue was taken up in pyridine (20 to 25 ml) and evaporated to dryness (repeated twice). Then the residue was dissolved in 30 ml dry dimethylformamide and evaporated to dryness (repeated three times). The dried residue was dissolved in 30 ml dimethylformamide and 0.97 ml diphenylphosphorochloridate (4.9 mmol) was added, followed by 1.6 ml tri-n-butylamine (3.25 mmol). The reaction mixture was stirred for 2 hr at room temperature and then evaporated to dryness. The residue was shaken with 70 ml dry diethyl ether for 2 min and then 150 ml petroleum ether was added. After 1 hr the yellow supernatant was decanted, leaving a yellow oil which was dissolved in 30 ml dry dimethylformamide and evaporated to dryness. The oil which remained was dissolved in 100 ml pyridine:dimethyl formamide (1:1 v/v) and one-half of this solution was reacted with the tri-n-octyl ammonium salt of ATP.

ATP (0.7 mmol) was converted to the pyridinium salt by chromatography on a 2.5×25 cm column of Dowex 50×2 in the pyridinium form. The aqueous solution of this salt was evaporated to dryness and 15 ml methanol and 1.4 ml tri-n-octylamine (1.4 mmol) were added. The mixture was stirred until the ATP dissolved and the solvent was removed under vacuum. The residue was dried by repeated evaporation from pyridine and then dry dimethylformamide. Finally, the oily residue was combined with the activated 2-[N-(2,4-dinitrophenyl)amino]ethylphosphate and the reaction mixture was stirred at room temperature overnight. Then the solvent was removed by evaporation under vacuum and the residue was stirred with 100 ml water for 1 hr, while the pH was maintained at 6.5 to 7.5 by addition of sodium hydroxide. The soluble material was applied to a 3×45 cm column of Sephadex A-50 (DEAE) in the bicarbonate form (available from Pharmacia Fine Chemicals, Piscataway, N.J. The chromatogram was developed with a linear gradient generated with 2 liters each 0.1M and 0.5M ammonium carbonate. Material which eluted between 0.18 and 0.26M ammonium carbonate was concentrated by evaporation under vacuum and the ammonium carbonate was removed by repeated evaporation to dryness from water. Further purification was carried out by thick-layer chromatography on silica gel with a solvent consisting of 7 parts ethanol to 3 parts 1M triethylammonium carbonate (pH 7.5). Two major yellow bands separated and were each scraped from the plate. The silica gel was stirred for 1 hr with methanol-water (1:1 v/v) and the soluble materials from each band were passed separately into 2.5×20 cm columns of DEAE-cellulose in the bicarbonate form. The columns were washed with water and then 0.5M ammonium carbonate. The yellow materials eluted by the salt were concentrated to dryness under vacuum. The compound which migrated faster on silica gel was identified as unreacted 2-[N-(2,4-dinitrophenyl)amino]ethylphosphate.

The second band, $R_f=0.64$, from the silica gel plate had optical absorption maxima at 257 and 259 nm, and the millimolar extinction coefficients of a solution in 0.02N hydrochloric acid were 21.1 and 16,2, respectively. This product, the desired conjugate, was found to contain 4.3 residues of phosphate per residue of ribose.

EXAMPLE 21

Direct binding-bioluminescent assay for antibody to 2,4-dinitrophenyl; use of ATP as labeling substance.

The bioluminescence reaction system used in this Example was based on the following reaction:

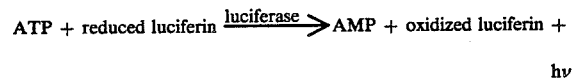

A light generating solution was prepared containing 10 mM morpholinopropane sulfonate buffer at pH 7.4, 10 mM magnesium sulfate, 0.7 mM luciferin and 0.15% (w/v) bovine serum albumin.

Nine specific binding reaction mixtures were prepared, each having a total volume of 10 μl and each containing 20 mM tris-(hydroxymethyl)-aminomethane hydrochloride buffer at pH 7.4, 10 mM ethylenediaminetetraacetic acid, 45 mM 2,4-dinitrophenyl-ATP conjugate (terminal phosphate derivative, prepared according to Example 20), and antiserum to 2,4-dinitrophenyl in the amounts indicated in Table 15. After incubation at 25° C. for 1.5 hour, duplicate 10 μl aliquots of each reaction mixture were assayed by injection into a 0.1 ml volume of the above-described light generating solution previously incubated at 25° C. for at least 2 minutes and contained in a test tube mounted in a Dupont Model 760 Bioluminescence Photometer (E. I. duPont de Nemours, Willmington, Del.).

Figure 9:
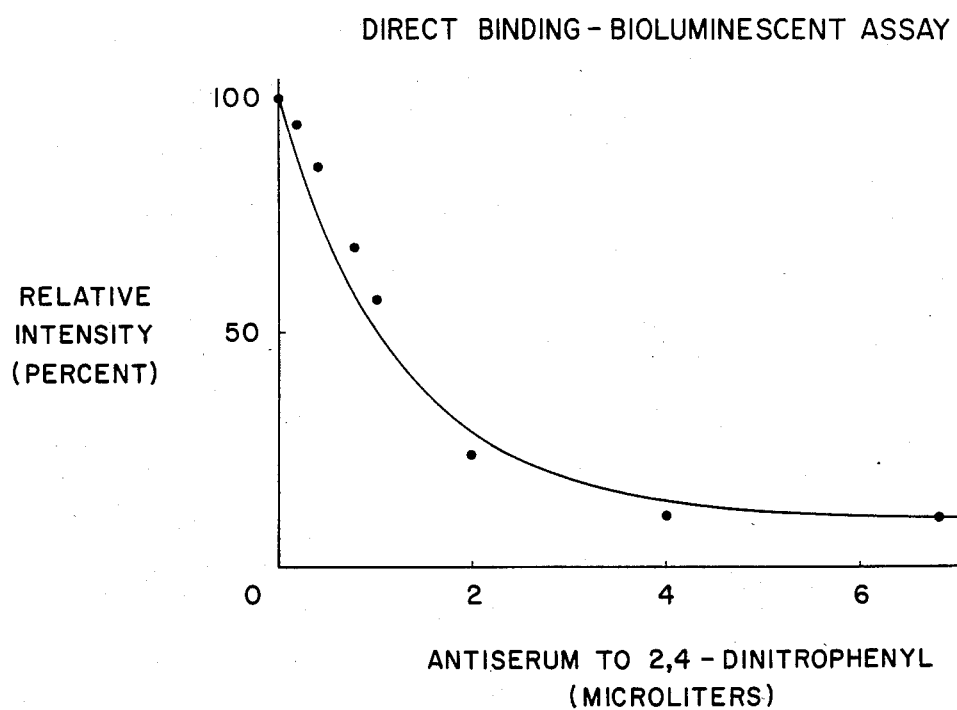
FIGS. 9 and 10, respectively, are graphical representations of the effect of various levels of two different ligands on the relative intensity of luminescence produced in direct and competitive binding-bioluminescent assay techniques.

The peak light intensity was read from the photometer. The average peak light intensity for each reaction mixture was calculated as well as the relative intensity (100% times the ratio of average peak intensity for the sample to that in the absence of antiserum). The results appear in Table 15 and in graphical form in FIG. 9 of the drawing.

TABLE 15

| reaction mixture | antiserum to 2,4-dinitrophenyl (μl) | average peak light intensity | relative intensity (percent) |
|---|---|---|---|
| 1 | 0 | 373 | 100 |
| 2 | 0.2 | 351 | 94 |
| 3 | 0.4 | 324 | 85 |
| 4 | 0.8 | 254 | 68 |
| 5 | 1.0 | 211 | 57 |
| 6 | 2.0 | 91 | 24 |
| 7 | 4.0 | 40 | 11 |
| 8 | 6.8 | 40 | 11 |
| 9 | 8.0 | 37 | 10 |

It was demonstrated in this Example that the activity of the ATP in the 2,4-dinitrophenyl-ATP conjugate relative to the bioluminescent reaction system was an inverse function of the amount of antiserum to 2,4-dinitrophenyl present in the reaction mixture. The present invention therefore provides a test composition and method for determining the ligand antibody to 2,4-dinitrophenyl in a liquid medium using a direct binding-bioluminescent assay technique.

EXAMPLE 22

Competitive binding-bioluminescent assay for derivatives of 2,4-dinitrophenyl; use of ATP as labeling substance.

The bioluminescence reaction system used in this Example was the same as that described in Example 21.

Figure 10:
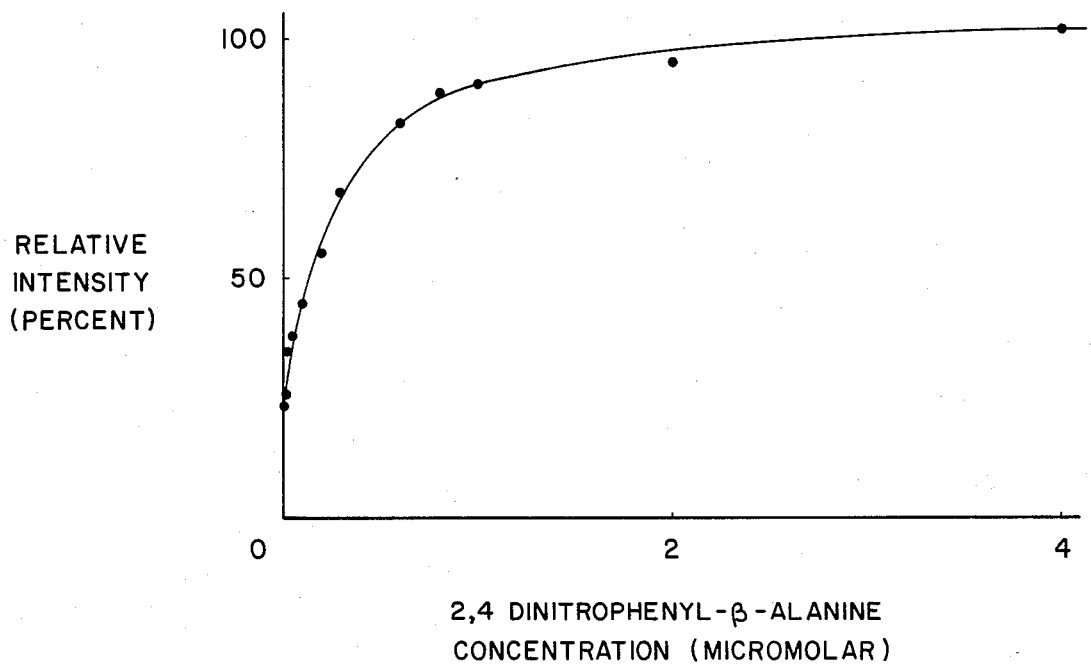

Thirteen specific binding reaction mixtures were prepared, each having a total volume of 100 μl and each containing 20 mM tris-(hydroxymethyl)-aminomethane hydrochloride buffer at pH 7.4, 10 mM ethylenediamine tetraacetic acid, 45 mM 2,4-dinitrophenyl-ATP conjugate (terminal phosphate derivative, prepared according to Example 20), and 2,4-dinitrophenyl-β-alanine at the concentrations indicated in Table 16. To twelve of the thirteen reaction mixtures (i.e. nos 2 through 13) was added an amount of antiserum to 2,4-dinitrophenyl sufficient to inhibit the peak light intensity produced by the bioluminescence reaction in the other reaction mixture (i.e. no. 1) by 75 percent. After incubation at 25° C. for 2 hours, duplicate 10 μl aliquots of each reaction mixture were assayed as in Example 21 and the average light intensity and relative intensity were calculated for each. The results appear in Table 16 and in graphical form in FIG. 10 of the drawing.

TABLE 16

| reaction mixture | concentration of 2,4-dinitrophenyl-β-alanine (μM) | average peak light intensity | relative intensity (percent) |
|---|---|---|---|
| 1 | 0.00 | 377 | 100 |
| 2 | 0.00 | 89 | 24 |
| 3 | 0.01 | 97 | 26 |
| 4 | 0.04 | 130 | 35 |
| 5 | 0.06 | 143 | 38 |
| 6 | 0.10 | 170 | 45 |
| 7 | 0.20 | 210 | 56 |
| 8 | 0.30 | 257 | 68 |
| 9 | 0.60 | 314 | 83 |
| 10 | 0.80 | 334 | 89 |
| 11 | 1.0 | 344 | 91 |
| 12 | 2.0 | 363 | 96 |
| 13 | 4.0 | 385 | 102 |

It was demonstrated in this Example that the relative intensity produced was a direct function of the amount of 2,4-dinitrophenyl-β-alanine present in the reaction mixture. The present invention therefore provides a test composition and method for determining ligands such as derivatives of 2,4-dinitrophenyl in a liquid medium using a competitive binding-bioluminescent assay technique.

EXAMPLE 23

Competitive binding-bioluminescent assay for derivatives of 2,4-dinitrophenyl; use of ATP as labeling substance.

The bioluminescence reaction system used in this Example was based on the following reaction:

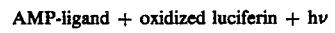

A. Assay using 6-position derivative of ATP.

Three specific binding reaction mixtures were prepared, each having a total volume of 100 μl and each containing 20 mM tris-(hydroxymethyl)-aminomethane hydrochloride buffer at pH 7.4, 10 mM ethylenediaminetetraacetic acid, 20 μl antiserum to 2,4-dinitrophenyl, 512 nM 2,4-dinitrophenyl-ATP conjugate (6-position derivative, prepared according to Example 18), and 2,4-dinitrophenyl-β-alanine at the concentrations indicated in Table 17. After incubation at 25° C. for 2 hours, duplicate 10 μl aliquots of each reaction mixture were assayed as in Example 21 and the average peak light intensity was calculated for each. The results appear in Table 17

TABLE 17

| reaction mixture | concentration of 2,4-dinitrophenyl-β-alanine (μM) | average peak light intensity |
|---|---|---|
| 1 | 0 | 7 |
| 2 | 25 | 14 |
| 3 | 2500 | 185 |

B. Assay using 8-position derivative of ATP.

Four specific binding reaction mixtures were prepared, each having a total volume of 100 μl and each containing 20 mM tris-(hydroxymethyl)-aminomethane hydrochloride buffer at pH 7.4, 10 mM ethylenediaminetetraacetic acid, 20 μl antiserum to 2,4-dinitrophenyl, 594 nM 2,4-dinitrophenyl-ATP conjugate (8-position derivative, prepared according to Example 19), and 2,4-dinitrophenyl-β-alanine at the concentrations indicated in Table 18. After incubation at 25° C. for 2 hours, duplicate 10 μl aliquots of each reaction mixture were assayed as in Example 21 and the average peak light intensity was calculated for each. The results appear in Table 18.

TABLE 18

| reaction mixture | concentration of 2,4-dinitrophenyl-β-alanine (μM) | average peak light intensity |
|---|---|---|
| 1 | 0 | 18 |
| 2 | 25 | 51 |
| 3 | 250 | 191 |
| 4 | 2500 | 190 |

The results of this Example and those of Example 22 demonstrate that the labeling substance, ATP, may be derivatized at various positions about its structure in the preparation of a useful conjugate for use in the specific binding assay method of the present invention.

EXAMPLE 24

Preparation of biotin-isoluminol conjugate.

6-(3-Biotinoylamido-2-hydroxypropylamine)-2,3-dihydrophthalazine-1,4-dione.

A. 4-(3-chloro-2-hydroxypropylamino)-N-methylphthalimide.

Twenty-five grams (0.142 mole) 4-amino-N-methylphthalamide, prepared according to the method described in *J. Chem. Soc.* 26: (1937), and 20.7 g (0.21 mole) 1-chloro-2,3-epoxypropane were added to 150 ml 2,2,2-trifluoroethanol and the reaction mixture was heated to reflux with stirring for 48 hrs. Seventy to eighty ml of 2,2,2-trifluoroethanol was removed by distillation and a heavy yellow precipitate formed when the remaining solution cooled to room temperature. This precipitate was triturated with ethyl acetate, collected by filtration and dried to give 29.5 g (77% yield) of the desired intermediate m.p. 136°-138.5° C. Calculated for $C_{12}H_{13}ClN_2O_3$: C, 53.64; H, 4.88; N, 10.45. Found: C, 53.87; H, 4.85; N, 10.81.

B. 4-[3-(N-Phthalmido)-2-hydroxypropylamino]-N-methylphthalimide.

The intermediate prepared in Part A (13.5 g, 0.05 mole) and 15.7 g (0.085 mole) potassium phthalimide were heated to reflux with stirring in 150 ml dimethylformamide for 24 hrs. The dimethylformamide was removed and the residue was washed with water and filtered. The yellow filter cake was recrystallized from acetic acid-water to give 12.8 g (67% yield) of product, m.p. 247°-248.5° C. Calculated for $C_{20}H_{17}N_3O_5$: C, 63.32; H, 4.52; N, 11.08. Found: C, 63.16; H, 4.38; N, 10.93.

C. 6-[3-Amino-2-hydroxypropylamino]-2,3-dihydrophalazine-1,4-dione.

The intermediate from Part B (5.0 g, 13.2 mmole), 90 ml absolute ethanol and 35 ml 95% hydrazine were refluxed with stirring for 4 hrs. The solvent was removed under a vacuum and the resulting solid was dried for 24 hrs under vacuum at 120° C. This material was stirred for 1 hr with 70 ml of 0.1N hydrochloric acid. The insoluble 2,3-dihydroxyphthalazine-1,4-dione was removed by filtration and the filtrate was adjusted to pH 6.5 with saturated sodium bicarbonate. The white precipitate which formed was collected by filtration and dried to give 2.2 g of the product (67% yield). After recrystallization from water, the compound decomposed at 273° C. Calculated for $C_{11}H_{14}N_2O_3$: C, 52.79; H, 5.64; N, 22.39. Found: C, 52.73; H, 5.72; N, 22.54.

D. Biotin-isoluminol conjugate.

Biotin (0.29 g, 1.2 mmole) and 0.17 ml triethylamine were dissolved in 20 ml dry dimethylformamide under anhydrous conditions and cooled to −10° C. A solution of 0.141 ml ethylchloroformate in 2.86 ml ether was added slowly and the reaction was stirred for 30 min. A precipitate which formed was separated by filtration. A suspension consisting of 600 mg (2.4 mmole) of the intermediate from Part C, 20 ml dry dimethylformamide and 1 ml dry pyridine was added to the filtrate quickly. This mixture was stirred at −10° C. for 30 min and then at room temperature overnight. During this period a solution was obtained. The dimethylformamide was removed by distillation at 60° C. and 0.10 mm Hg pressure. The oily residue was stirred with 50 ml 0.1N hydrochloric acid for 1 hr. A white solid which formed was filtered and washed with 0.1N hydrochloric acid and then water. After drying under a vacuum at room temperature overnight, 0.55 g (97% yield) of the product was obtained, m.p. 170°-3° C. Calculated for $C_{21}H_{28}N_6O_5S$: C, 52.92; H, 5.92; N, 17.64. Found: C, 51.69; H, 5.90; N, 17.63.

EXAMPLE 25

Specific binding-chemiluminescent assays; effect of avidin and biotin on activity of a biotin-isoluminol conjugate.

The chemiluminescent reaction system used in this example was based on the following reaction:

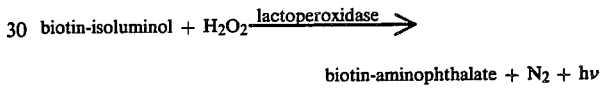

biotin-aminophthalate + $N_2$ + $h\nu$

Nine specific binding reaction mixtures were prepared, each having a total volume of 140 μl and each containing 0.1M tris-(hydroxymethyl)-aminomethane hydrochloride buffer at pH 7.4 and biotin, biotin-isoluminol conjugate (prepared according to Example 24), and avidin (added last) in the concentrations indicated in Table 19. After 5 minute incubation at 25° C., 10 μl 0.1M tris-(hydroxymethyl)aminomethane hydrochloride buffer at pH 7.4 containing 20 units/ml lactoperoxidase (available from Sigma Chemical Co., St. Louis, Mo.; assayed as described in *Methods in Enzymology* XVIIA, (1970) p. 653-Assay 2) was added to each reaction mixture. After incubation at 25° C. for 2 additional minutes, 10 μl 0.95 mM hydrogen peroxide in 10 mM tris-(hydroxymethyl)-aminomethane hydrochloride buffer at pH 7.4 was injected into each reaction mixture and the peak light intensity produced in each was measured using a Dupony Model 760 Bioluminescence Photometer (E. I. duPont de Nemours, Willmington, Del.). The results appear in Table 19.

TABLE 19

| reaction mixture | concentration of biotin (μM) | concentration of biotin-isoluminol conjugate (nM) | concentration of avidin (units/ml) | peak light intensity |
|---|---|---|---|---|
| 1 | — | — | — | 0.8 |
| 2 | — | — | 0.14 | 0.9 |
| 3 | — | 84 | — | 1.9 |
| 4 | — | 84 | 0.14 | 25.3 |
| 5 | 4 | — | — | 0.8 |
| 6 | 4 | 84 | — | 2.2 |
| 7 | 4 | — | 0.14 | 0.9 |
| 8 | 4 | 84 | 0.14 | 6.1 |
| 9 | 1.3 | 84 | 0.14 | 10.4 |

Reactions 1,2,5 and 7 were controls and show that in the absence of biotin-isoluminol conjugate, only a low background amount of light was measured. The result of reactions 3 and 6 indicate that the biotin-isoluminol conjugate was active in the chemilumescent reaction and that the presence of free biotin had no significant effect on such activity. The result of reaction 4 shows that in the presence of avidin, a binder for biotin, the activity of the biotin-isoluminol conjugate increased. This result is rather unexpected since one would anticipate that binding of avidin to the conjugate should limit the availability of the isoluminol moeity for the chemiluminescent reaction. The reason for the observed enhancement of light-production is not understood. A comparison of the results of reactions 4,8, and 9 demonstrate that the enhancement of light production is decreased inversely with the amount of free biotin present.

This Example demonstrates that the ligands avidin and biotin can be determined using specific binding-chemilumescent assay techniques and that according to the present invention the effect of binding between the labeling substance in the conjugate and a corresponding binding partner may be an enhancement, rather than inhibition, of the activity of the labeling substance.

EXAMPLE 26

Competitive binding-chemiluminescent assay for biotin; effect of various levels of biotin on the peak light intensity produced.

The chemiluminescent reaction system used in this Example was the same as that described in Example 25.

Six specific binding reaction mixtures were prepared, each having a total volume of 140 μl and each containing 0.1M tris-(hydroxymethyl)-aminomethane hydrochloride buffer at pH 7.4, 84 nM biotin-luminol conjugate (prepared as in Example 24), biotin at the concentrations indicated in Table 20, and 0.035 units/ml avidin (added last). After a 5 minute incubation at 25° C., 10 μl of lactoperoxidase (20 units/ml) were added to each reaction mixture.

Figure 11:
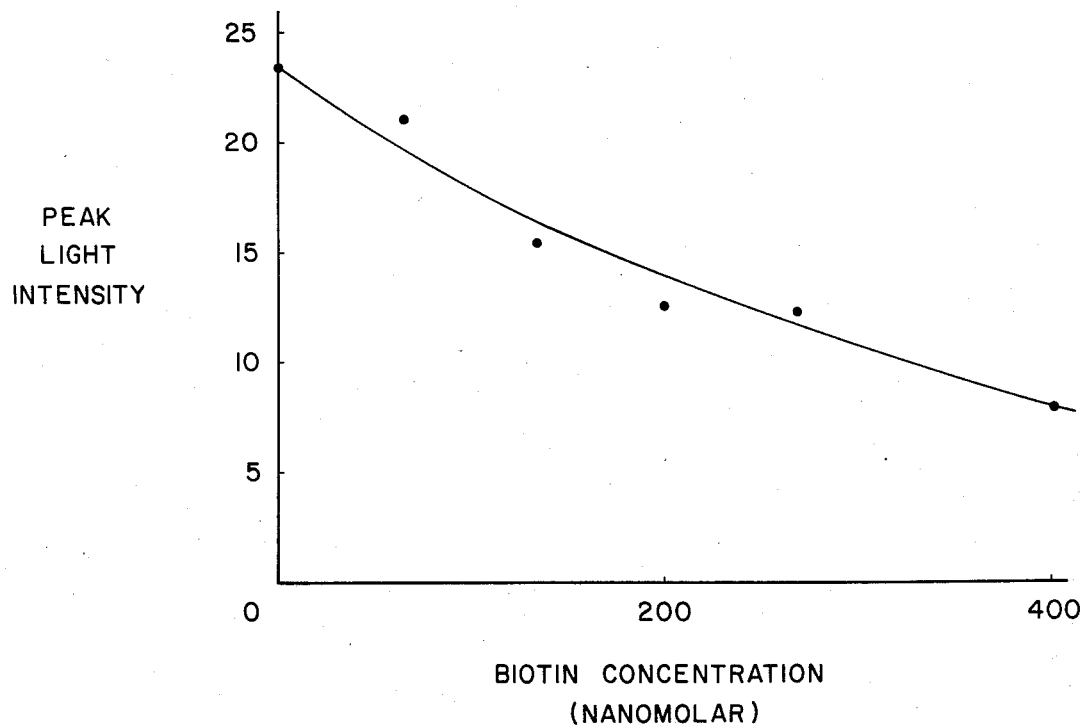
FIGS. 11 and 12, respectively, are graphical representations of the effect of various levels of a ligand on the peak light intensity produced in two different competitive binding-chemiluminescent assay techniques.

After an additional 2 minute incubation, 10 μl 0.95 mM hydrogen peroxide in 10 mM tris-(hydroxymethyl)-aminomethane hydrochloride buffer at pH 7.4 was injected into each reaction mixture and the peak light intensity produced in each was measured as in Example 25. The results appear in Table 20 and in graphical form in FIG. 11 of the drawing.

TABLE 20

| reaction mixture | concentration of biotin (nM) | peak light intensity |
| --- | --- | --- |
| 1 | 0 | 23.5 |
| 2 | 67 | 21.1 |
| 3 | 134 | 15.5 |
| 4 | 200 | 12.6 |
| 5 | 268 | 12.3 |
| 6 | 400 | 8.1 |

It was thus demonstrated that the magnitude of the peak light intensity produced by the chemiluminescent reaction system was an inverse function of the amount of biotin present in the specific binding reaction mixture. The present invention therefore provides a test composition and method for determining the presence of the ligand biotin in a liquid medium using a competitive binding-chemiluminescent assay technique.

EXAMPLE 27

Competitive binding-chemiluminescent assay for biotin.

The chemiluminescent reaction system used in this Example was based on the following reaction:

Figure 12:
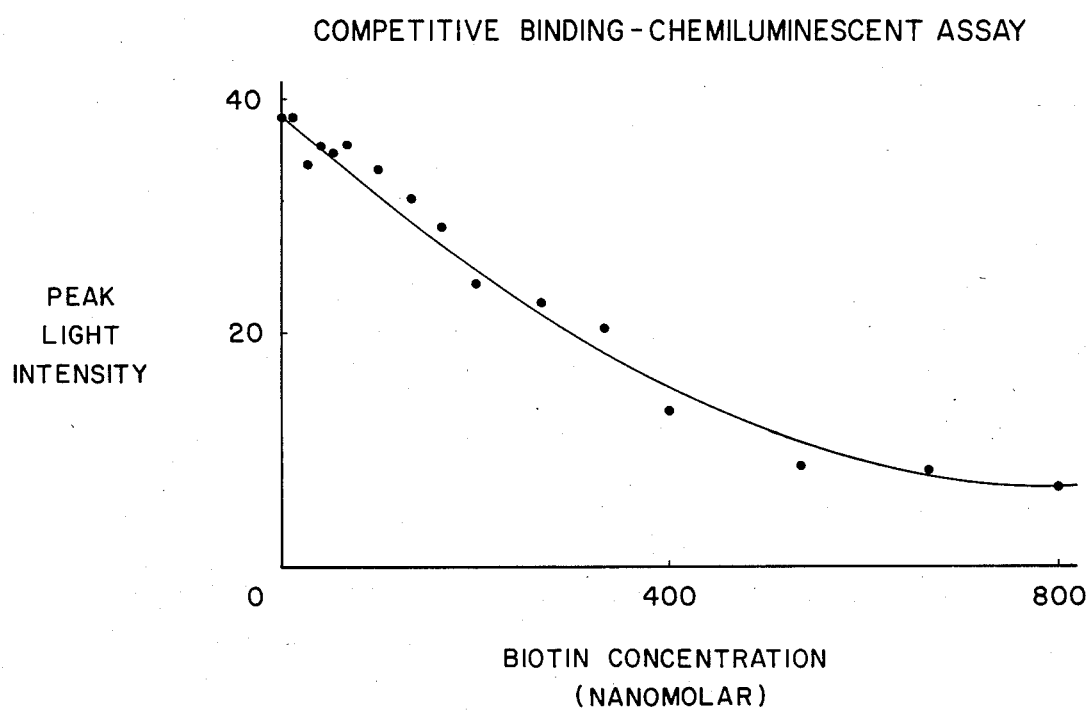

Sixteen specific binding reaction mixtures were prepared, each having a total volume of 150 μl and each containing 0.1M tris-(hydroxymethyl)-aminomethane hydrochloride at pH 8.0, 42 nM biotin-luminol conjugate (prepared as in Example 24), biotin at the concentrations indicated in Table 21, and 0.12 units/ml avidin (added last). After incubation at 25° C. for 5 minutes, 10 μl of dimethylformamide containing 0.15M potassium superoxide ($KO_2$) (available from Alpha Products, Beverly, Mass.) and 0.10M 1,4,7,10,13,16-hexaoxyacylcooctadecane (available from Aldrich Chemical Co., Milwaukee, Wisc.) were injected into each reaction mixture and the peak light intensity produced in each was measured as in Example 25. The results appear in Table 21 and in graphical form in FIG. 12 of the drawing.

TABLE 21

| reaction mixture | concentration of biotin (nM) | peak light intensity |
| --- | --- | --- |
| 1 | 0 | 38.5 |
| 2 | 13 | 38.5 |
| 3 | 27 | 34.3 |
| 4 | 40 | 36.1 |
| 5 | 53 | 35.2 |
| 6 | 67 | 36.2 |
| 7 | 101 | 34.0 |
| 8 | 133 | 31.7 |
| 9 | 166 | 29.1 |
| 10 | 200 | 24.2 |
| 11 | 267 | 22.8 |
| 12 | 333 | 20.5 |
| 13 | 400 | 13.4 |
| 14 | 534 | 8.6 |
| 15 | 667 | 8.3 |
| 16 | 800 | 7.0 |

It was demonstrated that the magnitude of the peak light intensity produced by the chemiluminescent reaction system was an inverse function of the amount of biotin present in the specific binding reaction mixture. The present invention therefore provides a test composition and method for determining the presence of the ligand biotin in a liquid medium using a competitive binding-chemiluminescent assay technique which does not employ an enzyme-catalyzed monitoring reaction.

What is claimed is:

1. A method for determining a ligand in a medium suspected of containing the ligand which comprises:
combining in an aqueous solution said medium, a reagent and a specific binding partner for the ligand in the medium, said reagent being a conjugate of said ligand or a specific binding analog thereof and a low molecular weight label compound having a bond enzymatically cleavable to produce a product distinguishable by a detectable signal and said enzymatic cleavage being substantially altered by binding of said reagent to said binding partner;
adding an enzyme capable of cleavage of said enzymatically cleavable bond; and analyzing for the effect of said medium on enzymatic cleavage of said bond by measuring said detectable signal.

2. The method of claim 1 wherein the label compound is a substrate for the enzyme.

3. The method of claim 2 wherein the enzymatic cleavage of the substrate is hydrolytic.

4. The method of claim 2 wherein the product formed by enzymatic cleavage of the substrate label compound is fluorescent.

5. The method of claim 2 wherein the substrate label compound includes a bridge group through which it is coupled to the ligand or analog thereof in the reagent and wherein the enzyme cleaves said bridge group to release said product distinguishable by a detectable signal.

6. The method of claim 5 wherein the released detectable molecule is fluorescent.

7. The method of claim 6 wherein the bridge group is an ester group, the enzyme is an esterase, and the released fluorescent molecule is umbelliferone or fluorescein, or a derivative thereof.

8. The method of claim 2 wherein the enzymatic cleavage of the substrate label compound is part of a cyclic reaction.

9. The method of claim 8 wherein the substrate label compound is a cycled reagent in the cyclic reaction.

10. The method of claim 8 wherein the cyclic reaction is exponential.

11. The method of claim 10 wherein the substrate label compound is a cycled reagent in the cyclic reaction.

12. The method of claim 1 wherein the label compound is a coenzyme for the enzyme.

13. The method of claim 12 wherein the coenzyme is a nucleotide coenzyme.

14. The method of claim 12 wherein the coenzyme is selected from the group consisting of the adenosine phosphates, nicotinamide adenine dinucleotide, and nicotinamide adenine dinucleotide phosphate.

15. The method of claim 12 wherein the coenzyme is nicotinamide adenine dinucleotide.

16. The method of claim 12 wherein the coenzyme is adenosine triphosphate.

17. The method of claim 12 wherein the coenzyme is flavin adenine dinucleotide.

18. The method of claim 12 wherein the enzymatic cleavage of the coenzyme label compound is part of a cyclic reaction as follows:

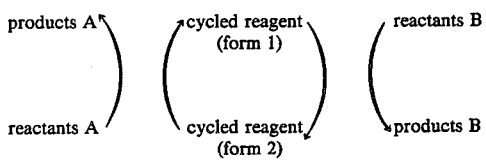

wherein the coenzyme label compound is comprised in one of reactants A, reactants B, and the cycled reagent.

19. The method of claim 18 wherein the coenzyme label compound is the cycled reagent.

20. The method of claim 19 wherein reactions A and B are catalyzed by the same enzyme.

21. The method of claim 20 wherein the cycled coenzyme label compound cycles between oxidized and reduced forms.

22. The method of claim 21 wherein the coenzyme is flavin adenine dinucleotide.

23. The method of claim 18 wherein the cyclic reaction is exponential.

24. The method of claim 23 wherein the coenzyme label compound is the cycled reagent.

25. The method of claim 1 wherein the reagent, the binding partner, and the enzyme are combined with the medium substantially simultaneously.

26. The method of claim 1 wherein the medium is combined with the binding partner and the enzyme and thereafter with the reagent.

27. The method of claim 1 wherein the label compound has a molecular weight of less than 9000.

28. The method of claim 1 wherein the ligand is selected from the group consisting of antigens and antibodies thereto; haptens and antibodies thereto; and hormones, vitamins, metabolites, and pharmacological agents, and their receptors and binding substances.

29. The method of claim 1 wherein the ligand is a hapten or an antigen and the specific binding partner is an antibody thereto.

30. The method of claim 1 wherein said enzymatic cleavage is substantially inhibited by binding of said reagent to said binding partner.

31. The method of claim 1 wherein the medium under assay is a biological fluid.

32. A method for determining a ligand in a medium suspected of containing the ligand which comprises:
combining in an aqueous solution said medium and a reagent which is a conjugate of a specific binding partner for the ligand and a low molecular weight label compound having a bond enzymatically cleavable to produce a product distinguishable by a detectable signal and said enzymatic cleavage being substantially altered by binding of said reagent to said ligand;
adding an enzyme capable of cleavage of said enzyamtically cleavable bond; and
analyzing for the effect of said medium an enzymatic cleavage of said bond by measuring said detectable signal.

33. The method of claim 32 wherein the label compound is a substrate for the enzyme.

34. The method of claim 33 wherein the enzymatic cleavage of the substrate is hydrolytic.

35. The method of claim 32 wherein the label compound is a coenzyme for the enzyme.

36. The method of claim 32 wherein the label compound has a molecular weight of less than 9000.

37. The method of claim 33 wherein the ligand is an antibody.

38. The method of claim 32 wherein said enzymatic cleavage is substantially inhibited by binding of said reagent to said ligand.

39. A method for determining the presence of a protein in a medium suspected of containing the protein which comprises:
combining in an aqueous solution said medium, a reagent and an antibody for the protein in the medium, said reagent being a conjugate of said protein and a low molecular weight compound having a bond enzymatically cleavable by hydrolysis to produce a product distinguishable by a detectable signal and said enzymatic cleavage by hydrolysis being substantially inhibited by binding of said reagent to said antibody;

adding an enzyme capable of hydrolytic cleavage of said enzymatically cleavable bond; and analyzing for the effect of said medium on enzyme cleavage of said bond by measuring said detectable signal.

40. The method of claim 39 wherein said product is fluorescent.

41. The method of claim 39 wherein said bond is a bridge group that undergoes said hydrolytic enzyme cleavage to produce said product.

42. The method of claim 41 wherein said bridge group is an ester group and said enzyme is an esterase.

* * * * *

UNITED STATES PATENT AND TRADEMARK OFFICE
CERTIFICATE OF CORRECTION

PATENT NO. : 4,629,688
DATED     : December 16, 1986
INVENTOR(S) : Robert C. Boguslaski et al.

It is certified that error appears in the above-identified patent and that said Letters Patent is hereby corrected as shown below:

On the title page, the first inventor's name should read
-- Robert C. Boguslaski --.

Signed and Sealed this

Fourteenth Day of April, 1987

*Attest:*

DONALD J. QUIGG

*Attesting Officer*    *Commissioner of Patents and Trademarks*